United States Patent [19]
Laufer et al.

[11] Patent Number: 6,135,997
[45] Date of Patent: Oct. 24, 2000

[54] METHOD FOR TREATING HEMORRHOIDS

[75] Inventors: Michael D. Laufer, Menlo Park; Brian E. Farley, Los Altos, both of Calif.

[73] Assignee: Vnus Medical Technologies, Inc., Sunnyvale, Calif.

[21] Appl. No.: 09/193,319

[22] Filed: Nov. 16, 1998

Related U.S. Application Data

[60] Division of application No. 08/720,209, Sep. 26, 1996, and a continuation-in-part of application No. 08/610,911, Mar. 5, 1996, Pat. No. 6,036,687.

[51] Int. Cl.$^7$ .................................................. A61B 18/04
[52] U.S. Cl. .............................. 606/27; 606/32; 604/20; 604/113; 604/500
[58] Field of Search .................................. 606/27, 40, 32; 604/104–107, 19–21, 93; 607/1, 2, 96, 101, 103, 122; 600/9, 11

[56] References Cited

U.S. PATENT DOCUMENTS

| | | |
|---|---|---|
| 373,399 | 11/1887 | Hamilton . |
| 659,409 | 10/1900 | Mosher . |
| 833,759 | 10/1906 | Sourwine . |
| 985,865 | 3/1911 | Turner, Jr. . |

(List continued on next page.)

FOREIGN PATENT DOCUMENTS

| | | |
|---|---|---|
| 0 189 329 A2 | 7/1986 | European Pat. Off. . |
| 0 629 382 A1 | 12/1994 | European Pat. Off. . |
| 0 738 501 A1 | 10/1996 | European Pat. Off. . |
| WO92/12681 | 8/1992 | WIPO . |
| WO 93/21846 | 11/1993 | WIPO . |
| WO 94/07446 | 4/1994 | WIPO . |
| WO 94/21170 | 9/1994 | WIPO . |
| WO 95/02370 | 1/1995 | WIPO . |
| WO 95/10236 | 4/1995 | WIPO . |
| WO 95/10322 | 4/1995 | WIPO . |
| WO 95/31142 | 11/1995 | WIPO . |
| WO 96/32885 | 10/1996 | WIPO . |
| WO 97/17892 | 5/1997 | WIPO . |

OTHER PUBLICATIONS

Watts, G.T., Endovenous Diathermy Destruction of Internal Saphenous, British Medical Journal, Oct. 7, 1972, p. 53.

O'Reilly, Kevin, Endovenous Diathermy Sclerosis of Varicose Veins, The Australian, New Zealand Journal of Surgery, vol. 47, No. 3, Jun. 1977, pp. 393–395.

O'Reilly, Kevin, A Technique of Diathermy Sclerosis of Varicose Veins, The Australian, New Zealand Journal of Surgery, vol. 51, No. 4, Aug. 1981, pp. 379–382.

Cragg et al., Endovascular Diathermic Vessel Occlusion, Diagnostic Radiology, 144: 303–308, Jul. 1982.

Gradman, Venoscopic Obliteration of Variceal Tributaries Using Monopolar Electrocautery, Journal of Dermatology Surgery Oncology, 1994, 20, p. 482–485.

Inturri, Pathophysiology of Portal Hypertension, Journal of Vascular Technology 19 (5–6):271–276, Sep.–Dec. 1995.

(List continued on next page.)

*Primary Examiner*—Corrine McDermott
*Assistant Examiner*—Cris L. Rodriguez
*Attorney, Agent, or Firm*—Fulwider Patton Lee & Utecht, LLP

[57] ABSTRACT

A catheter delivers an electrode within a vein for a minimally invasive treatment of hemorrhoids using RF energy. The catheter is introduced into a patient and positioned within the section of the vein to be treated. The electrode radiates high frequency energy towards the vein, and the surrounding venous tissue becomes heated and begins to shrink. The catheter includes a controllable member for limiting the amount of shrinkage of the vein to the diameter of the member. The electrode remains active until there has been sufficient shrinkage of the vein. The extent of shrinkage of the vein can be detected by fluoroscopy. After treating one section of the vein, the catheter and the electrode can be repositioned within the hemorrhoidal venous system to treat different sections until all desired venous sections and valves are repaired and rendered functionally competent. Shrinkage of the vein further thickens and stiffens the vein wall which reduces the potential for the hemorrhoid vein to dilate.

71 Claims, 10 Drawing Sheets

U.S. PATENT DOCUMENTS

| | | |
|---|---|---|
| 3,230,957 | 1/1966 | Seifert . |
| 3,301,258 | 1/1967 | Werner et al. . |
| 3,557,794 | 1/1971 | Van Patten . |
| 3,920,021 | 11/1975 | Hiltebrandt . |
| 4,016,886 | 4/1977 | Doss et al. . |
| 4,043,338 | 8/1977 | Homm et al. . |
| 4,119,102 | 10/1978 | LeVeen . |
| 4,154,246 | 5/1979 | LeVeen . |
| 4,312,364 | 1/1982 | Covnert et al. . |
| 4,346,715 | 8/1982 | Gammell . |
| 4,522,205 | 6/1985 | Taylor et al. . |
| 4,643,186 | 2/1987 | Rosen et al. . |
| 4,660,571 | 4/1987 | Hess et al. . |
| 4,664,120 | 5/1987 | Hess . |
| 4,672,962 | 6/1987 | Hershenson ............................ 128/303.1 |
| 4,699,147 | 10/1987 | Chilson et al. . |
| 4,709,698 | 12/1987 | Johnston et al. . |
| 4,748,979 | 6/1988 | Hershenson ............................ 128/303.1 |
| 4,765,331 | 8/1988 | Petruzzi et al. ..................... 128/303.14 |
| 4,776,349 | 10/1988 | Nashef et al. . |
| 4,807,620 | 2/1989 | Strul et al. . |
| 4,823,791 | 4/1989 | D'Amelio et al. .................. 123/303.14 |
| 4,823,812 | 4/1989 | Eshel et al. .............................. 128/804 |
| 4,936,842 | 6/1990 | D'Amelio et al. ......................... 606/42 |
| 4,945,912 | 8/1990 | Langberg . |
| 4,966,597 | 10/1990 | Cosman . |
| 4,976,711 | 12/1990 | Parins et al. . |
| 4,979,948 | 12/1990 | Geddes et al. . |
| 5,010,894 | 4/1991 | Edhag . |
| 5,035,694 | 7/1991 | Kasprzyk . |
| 5,057,107 | 10/1991 | Parins et al. . |
| 5,078,717 | 1/1992 | Parins et al. . |
| 5,098,429 | 3/1992 | Sterzer . |
| 5,117,828 | 6/1992 | Metzger et al. . |
| 5,122,137 | 6/1992 | Lennox . |
| 5,156,151 | 10/1992 | Imran . |
| 5,188,602 | 2/1993 | Nichols . |
| 5,190,517 | 3/1993 | Zieve et al. . |
| 5,215,103 | 6/1993 | Desai . |
| 5,255,678 | 10/1993 | Deslauriers et al. . |
| 5,263,493 | 11/1993 | Avitall . |
| 5,275,610 | 1/1994 | Eberbach . |
| 5,281,218 | 1/1994 | Imran . |
| 5,293,869 | 3/1994 | Edwards et al. . |
| 5,314,466 | 5/1994 | Stern et al. . |
| 5,370,677 | 12/1994 | Rudie et al. . |
| 5,370,678 | 12/1994 | Edwards et al. . |
| 5,383,917 | 1/1995 | Desai et al. . |
| 5,397,339 | 3/1995 | Desai . |
| 5,403,312 | 4/1995 | Yates et al. . |
| 5,405,322 | 4/1995 | Lennox et al. . |
| 5,405,346 | 4/1995 | Grundy et al. . |
| 5,409,000 | 4/1995 | Imran . |
| 5,411,025 | 5/1995 | Webster, Jr. . |
| 5,423,815 | 6/1995 | Fugo . |
| 5,431,649 | 7/1995 | Mulier et al. . |
| 5,437,664 | 8/1995 | Cohen et al. . |
| 5,447,529 | 9/1995 | Marchlinski et al. . |
| 5,449,381 | 9/1995 | Imran . |
| 5,454,809 | 10/1995 | Janssen . |
| 5,458,596 | 10/1995 | Lax et al. . |
| 5,462,545 | 10/1995 | Wang et al. . |
| 5,465,717 | 11/1995 | Imran et al. . |
| 5,472,441 | 12/1995 | Edwards et al. . |
| 5,505,730 | 4/1996 | Edwards . |
| 5,514,130 | 5/1996 | Baker . |
| 5,545,161 | 8/1996 | Imran . |
| 5,556,396 | 9/1996 | Cohen et al. . |
| 5,570,692 | 11/1996 | Morinaga ........................... 128/662.05 |
| 5,709,224 | 1/1998 | Behl et al. . |
| 5,810,804 | 9/1998 | Gough et al. . |
| 5,817,092 | 10/1998 | Behl . |
| 5,827,268 | 10/1998 | Laufer . |
| 5,863,290 | 1/1999 | Gough et al. . |
| 5,868,740 | 2/1999 | LaVeen et al. . |
| 5,879,347 | 3/1999 | Aaadat ...................................... 606/28 |
| 5,891,134 | 4/1999 | Goble et al. .............................. 606/27 |
| 5,897,553 | 4/1999 | Mulier et al. ............................. 606/41 |
| 6,014,589 | 1/2000 | Farley et al. ............................. 604/98 |
| 6,024,742 | 1/2000 | Tu et al. ................................... 606/41 |

OTHER PUBLICATIONS

Don Crockett, Jr., M.D., et al., Preliminary Experience with an Endovascular Catheter for Electrocoagulation of Peripheral Veins, The Journal of Vascular Technology, Winter 1996, at 19–22.

Samuel R. Money, M.D., Endovascular Electroablation of Peripheral Veins, 22 Annual Symposium, Current Critical Problems, New Horizons and Techniques in Vascular and Endovascular Surgery (Nov. 1995).

Kevin O'Reilly, Endovenous Diathermy Sclerosis AE a Unit of the Armamentarium for the Attack on Varicose Veins, The Medical Jourrnal of Australia, Jun. 1, 1974, at 900.

Francis Brunelle, M.D., et al., A Bipolar Electrode for Vascular Electrocoagulation with Alternating Current, Technical Notes, Oct. 1980, at 239–240.

Yutaka Ogawa, M.D., et al., Electrothrombosis as a Treatment of Cirsoid Angioma in the Face and Scalp and Varicosis of the Leg, Plastic and Reconstructive Surgery, Sep. 1982, vol. 3, at 310–318.

Harold Aaron, M.D., et al., The Medical Letter on Drugs and Therapeutics, Jul. 12, 1968, at 53–55.

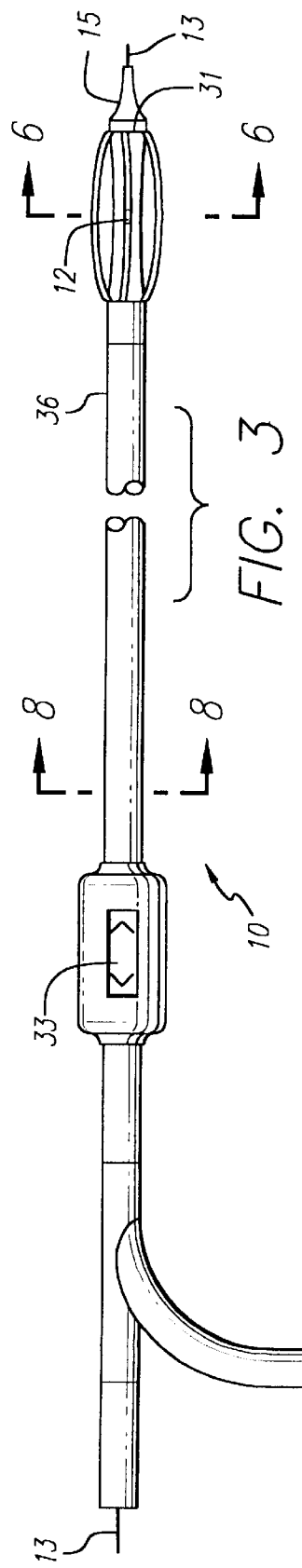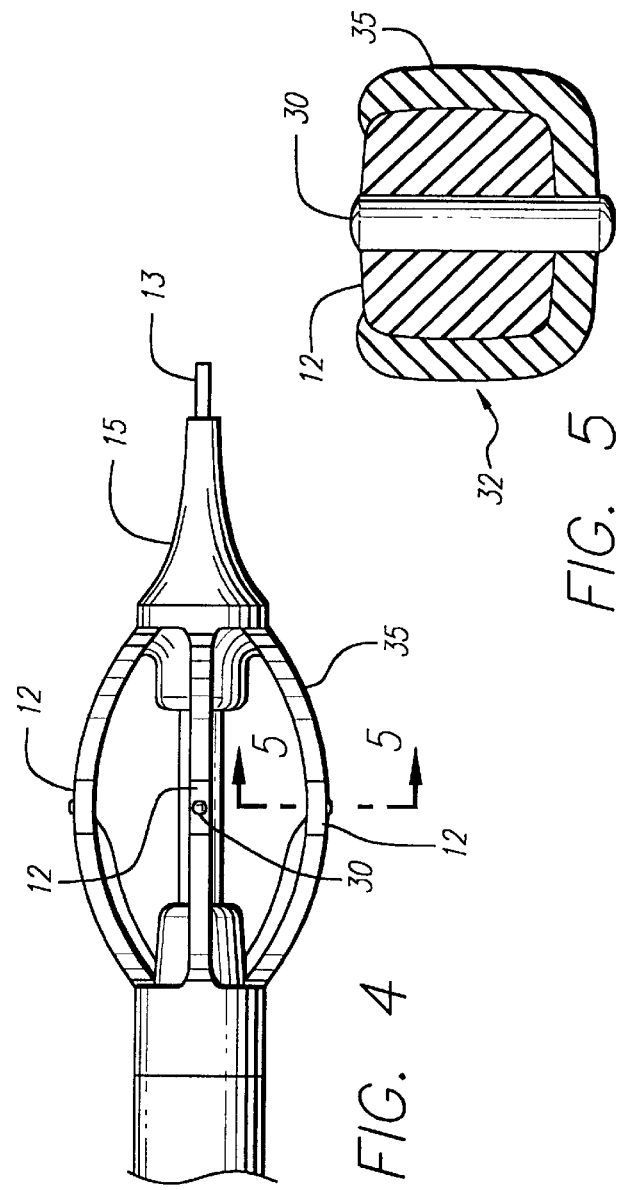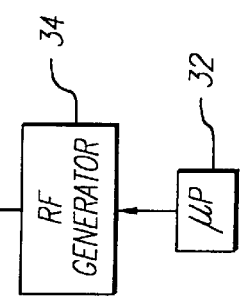
FIG. 3
FIG. 4
FIG. 5

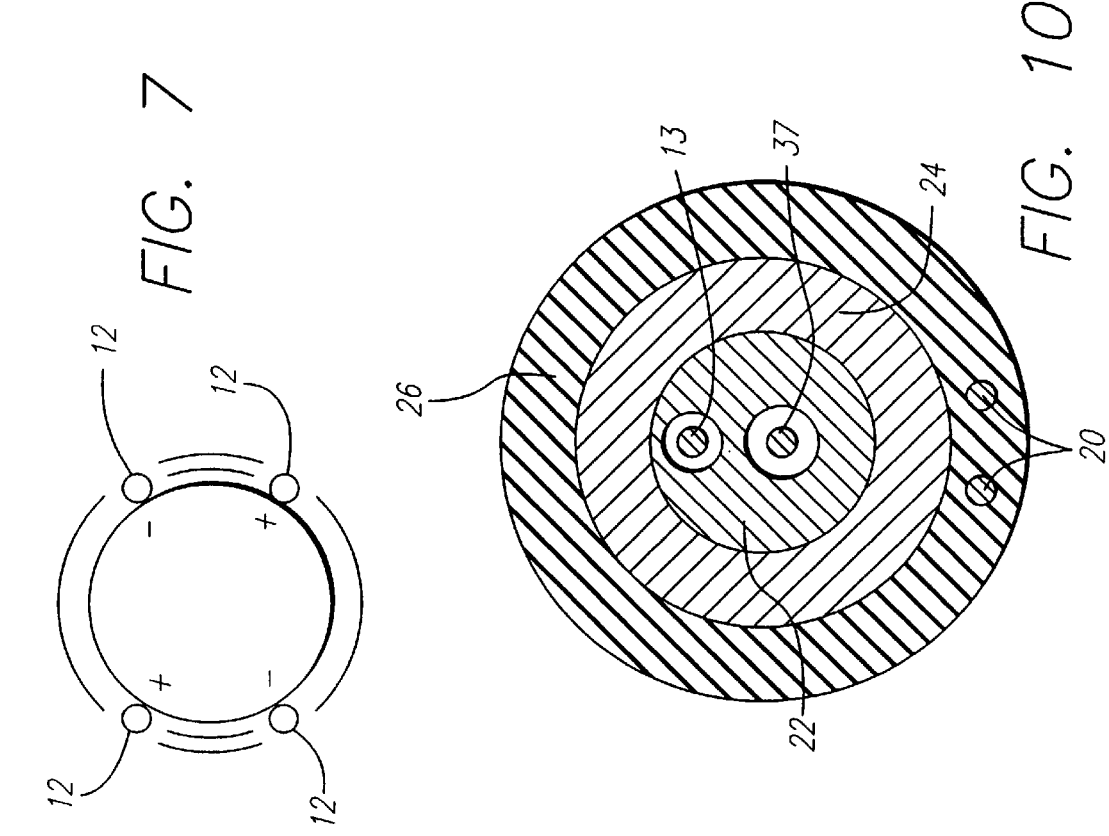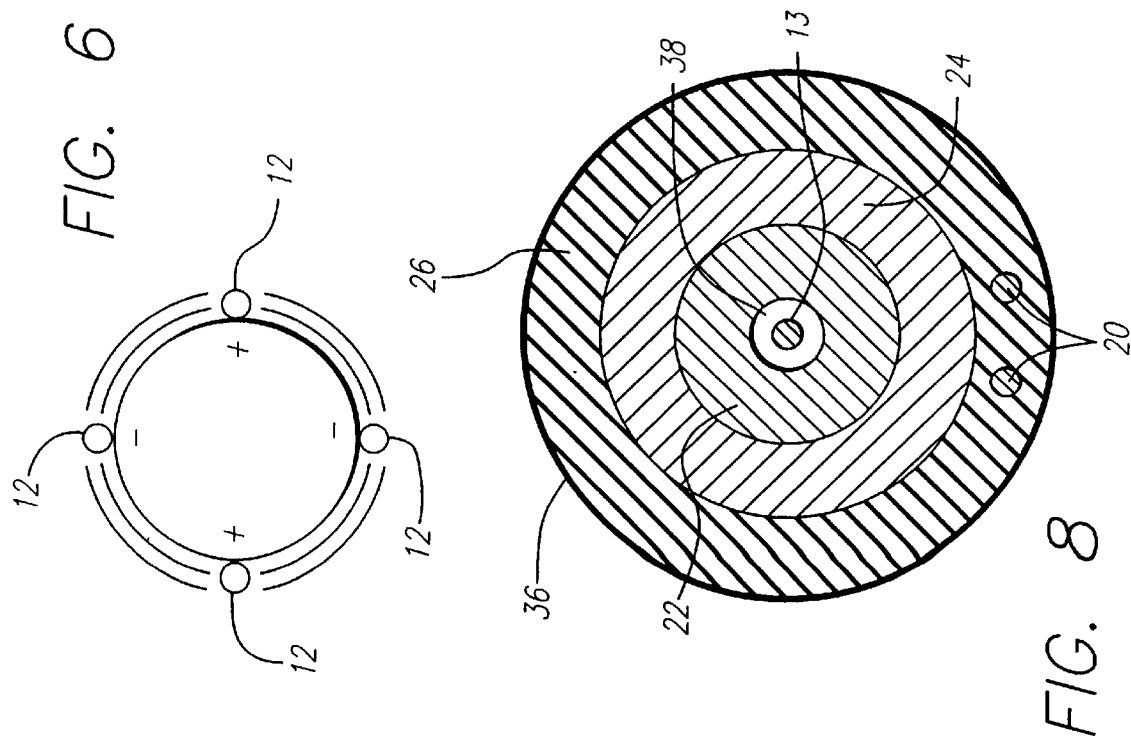

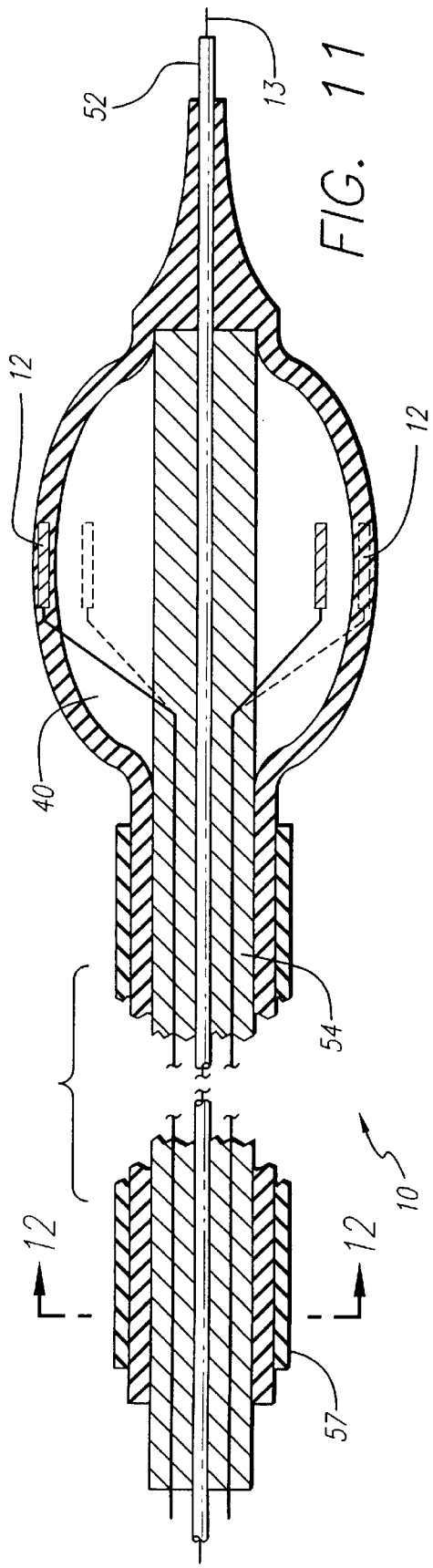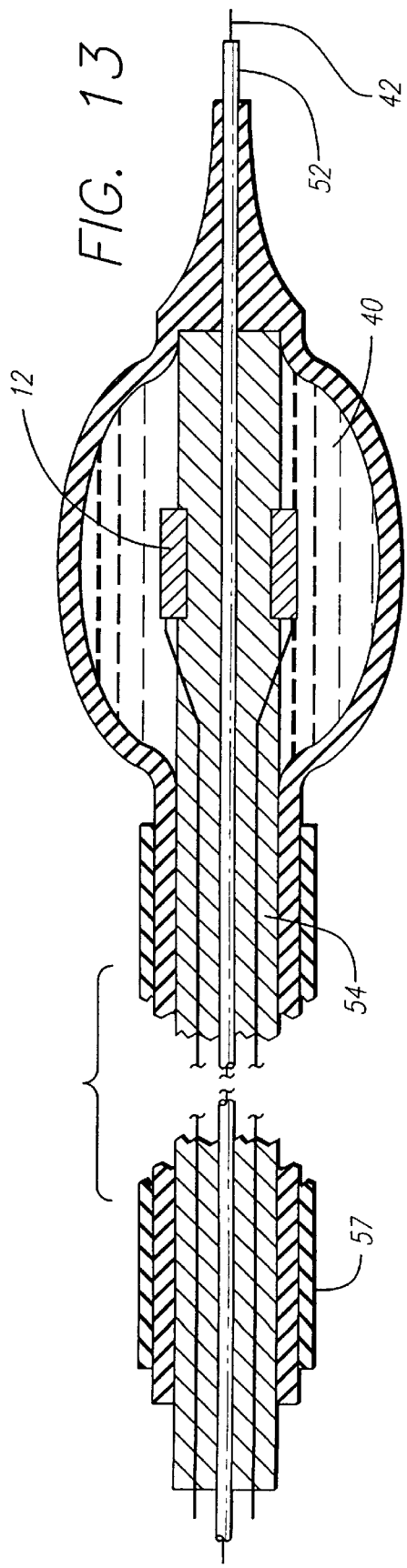

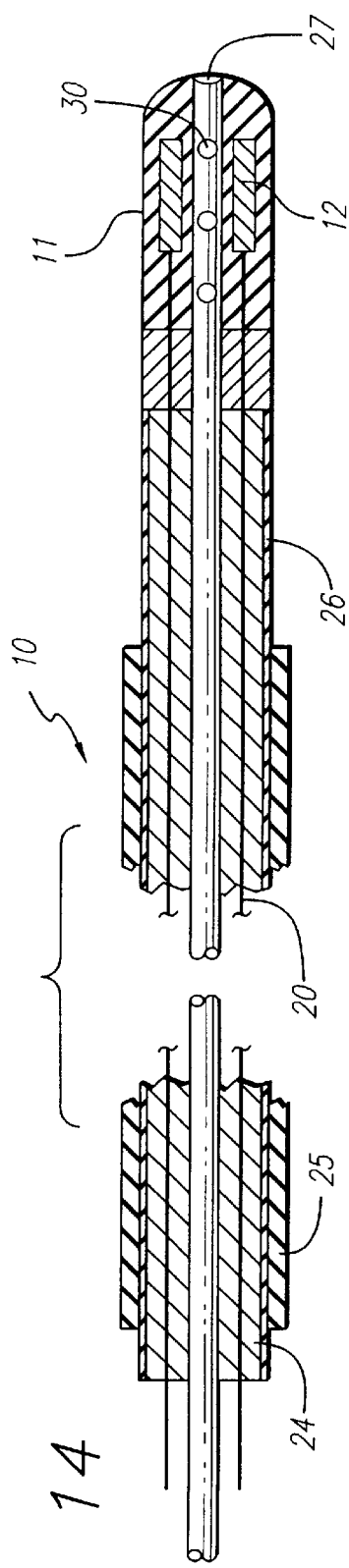
FIG. 14
FIG. 15
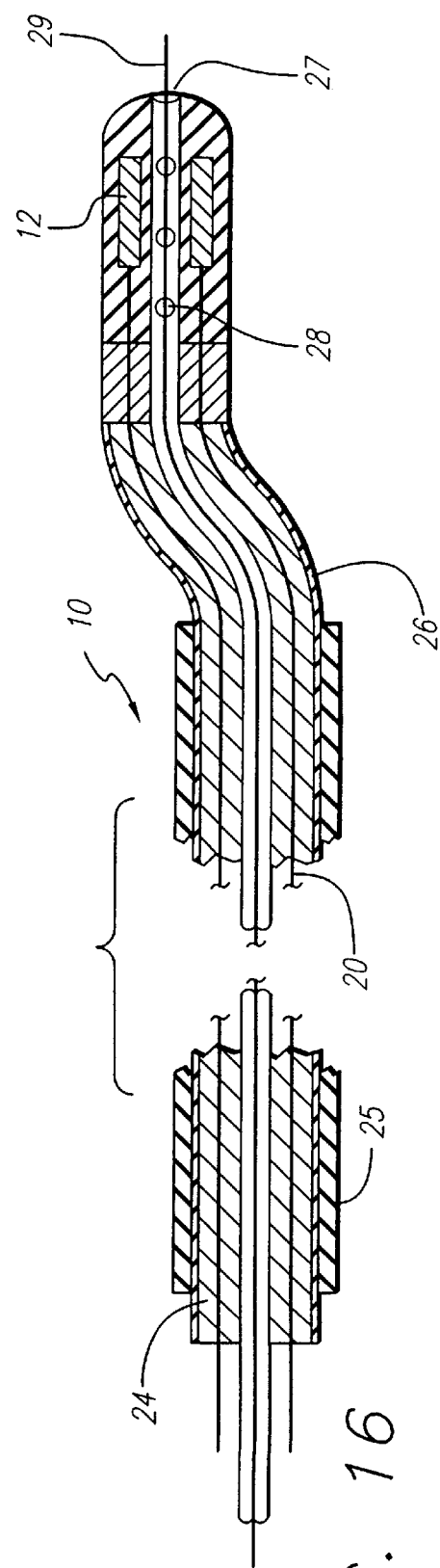
FIG. 16

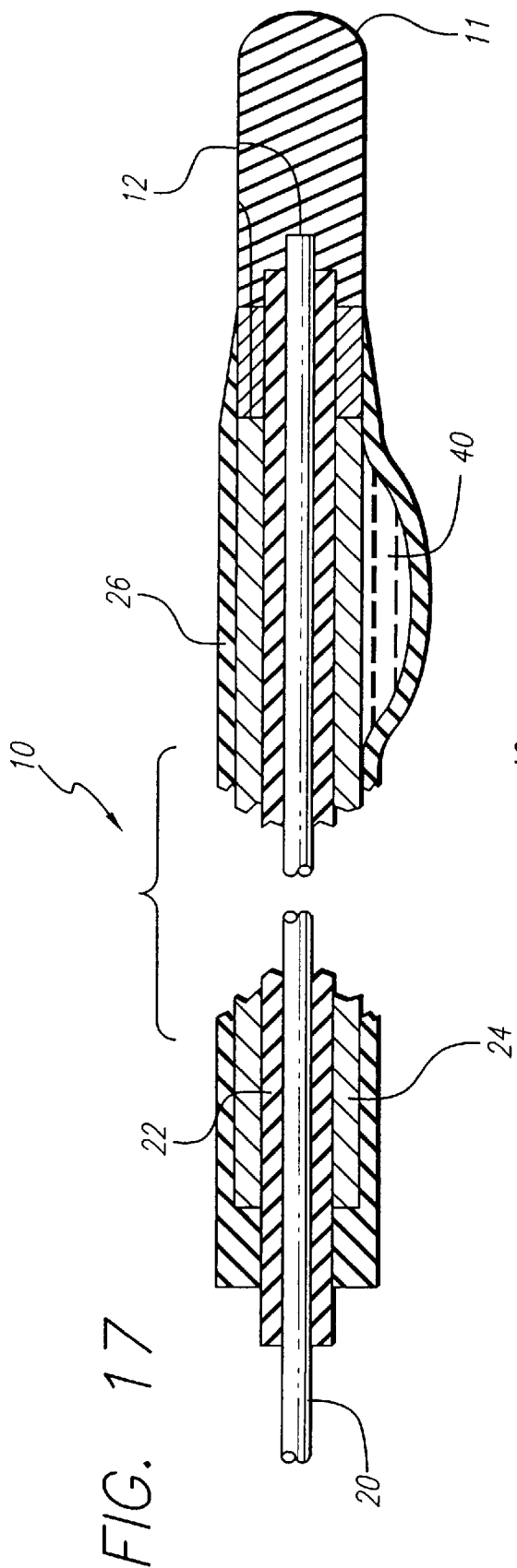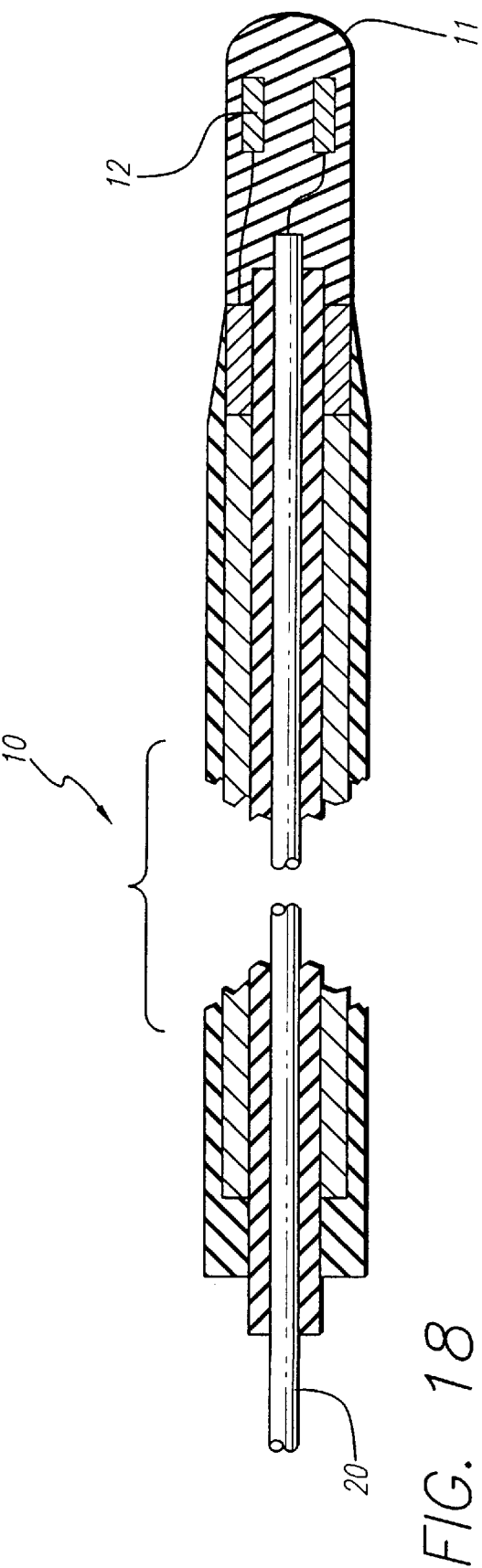

METHOD FOR TREATING HEMORRHOIDS

This application is a divisional of application Ser. No. 08/720,209, filed on Sep. 26, 1996, and a continuation-in-part of application Ser. No. 08/610,911, filed on Mar. 5, 1996 now U.S. Pat. No. 6,036,687. Application Ser. No. 08/720,209 is hereby incorporated by reference.

BACKGROUND OF THE INVENTION

This invention relates to the treatment and correction of hemorrhoids, and more particularly to a minimally invasive procedure using a catheter-based system to intravenously deploy one or more electrodes for providing radio frequency (RF) energy, microwave energy, or thermal energy to shrink a dilated vein in order to change the fluid flow dynamics and to restore the competency of the venous valve and the proper function of the vein.

Incompetent valves in the venous system can occur with vein dilation. Separation of the cusps of the venous valve at the commissure may occur as a result thereby leading to incompetence. Another cause of valvular incompetence occurs when the leaflets are loose and elongated. Loose leaflets of the venous valve results in redundancy, which allows the leaflets to fold on themselves and leave the valve open. These loose leaflets may prolapse, resulting in reflux of blood in the vein. When the venous valve fails, there is an increased strain and pressure on the lower venous sections and overlying tissues sometimes leading to additional valvular failure.

Hemorrhoids are a common ailment involving dilated veins which can result in bleeding, itching, and pain. Hemorrhoids are dilated veins in and around the anus and lower rectum. Dilation may result from an increased pressure in the hemorrhoidal vein. Constipation, including the frequent straining to pass hard stools increases pressure in hemorrhoidal veins, is a common cause of hemorrhoids. Other contributing factors include pregnancy, a low fiber diet, and obesity. As the hemorrhoidal vein becomes more dilated from the increased pressure, the venous valves of the hemorrhoidal vein may begin to fail and become incompetent. This can exacerbate the dilation of the hemorrhoidal vein as reflux of blood is allowed in the vein by the open incompetent valve. The vein may eventually form a sac-like protrusion if the condition is allowed to persist. Hemorrhoids are generally classified as being either internal or external, depending on their location relative to the dentate line. The dentate line is easily identified as the demarcation between the pink mucosa that form the anoderm. The dentate line separates the internal and external hemorrhoid systems. Internal hemorrhoids are located inside the anus above the dentate line. External hemorrhoids are located below the dentate line. Either can extend out of the anus.

Straining or irritation caused by passing stool can injure the delicate surface of an internal hemorrhoid and cause bleeding. If the pressure and dilation of the hemorrhoidal vein continues, the internal hemorrhoids may prolapse and be forced through the anal opening. If a hemorrhoid remains prolapsed, considerable discomfort, including itching and bleeding, may result. The blood supply to these prolapsed hemorrhoids may become cut off by the anal sphincter, which gives rise to a strangulated hemorrhoid. Thrombosis may result where the blood within the prolapsed vein becomes clotted. This extremely painful condition can cause edema and inflammation.

Increased pressure in the portal venous system can also cause an increase in pressure of the superior hemorrhoidal vein (SHV) leading to an increased diameter of the hemorrhoid. The portal venous system allows venous drainage from the intestinal tissues to the liver, and can become hypertensive when the lever is cirrhotic.

The treatment methods for hemorrhoids include invasive surgery to remove the hemorrhoid, elastic ring ligation, sclerotherapy, and the application of topical ointments or suppositories. The surgical removal of extensive or severe hemorrhoids is known as a hemorrhoidectomy. This surgical procedure can be used on both internal and external hemorrhoids. However, such surgery typically involves a long recovery period, along with the associated risks and expense of invasive surgery.

Internal hemorrhoids may be treated by rubber band ligation, where a legator is inserted through a scope in the anal canal. The hemorrhoid is grasped with forceps in the legator and held in position. The legator includes a cylinder which is slid upwards and releases one or more rubber bands around the base of the hemorrhoid. A typical diameter for the rubber band is one millimeter. The band cuts off the circulation of blood to the hemorrhoid, and the hemorrhoid begins to wither away. Provided the rubber band remains in place, the hemorrhoid typically drops off within seven to ten days.

Sclerotherapy, another treatment for hemorrhoids, involves injecting a solution, such as sodium morrhuate or phenol oil, submucously into the areolar tissue around the hemorrhoidal vein to cause inflammation and scarring to eliminate the hemorrhoid. Other external treatments cause burning or coagulation to destroy the hemorrhoid. In infrared coagulation, infrared light may be applied to create a small tissue-destroying burn around the base of the hemorrhoid to cut off the blood supply to the hemorrhoid. Electrocoagulation, sometimes referred to as bipolar diathermy, may be utilized in a similar manner. In laser therapy, also known as vaporization, a laser beam causes a superficial burn to seal off the blood vessels and retain the hemorrhoid in a non-prolapsed position.

The prior treatments for hemorrhoids involving external ligation or excision of the hemorrhoid may not affect the underlying causes which gave rise to the hemorrhoidal condition initially. Thus the condition may recur.

A need exists in the art to treat dilated hemorrhoidal veins to reduce venous pressure on the hemorrhoidal region. Such treatment should maintain the functional patency of the vein and restore valvular competency at the origins of the hemorrhoids as well as within the hemorrhoid itself.

SUMMARY OF THE INVENTION

Briefly, and in general terms, the present invention provides a minimally invasive method for solving the underlying problems of hemorrhoids, and uses a novel repair system, including a catheter for placing means for heating within a vein. The present invention includes a method of applying energy to cause shrinkage of a vein for treating hemorrhoids, the method comprising the steps of introducing a catheter having a working end and means for heating located at the working end, to a treatment site in a vein; positioning the means for heating at the treatment site in the vein; applying energy from the means for heating to controllably heat the treatment site and cause shrinkage of the vein; and terminating the emission of energy from the means for heating after sufficient shrinkage of the vein has occurred so as to reduce venous pressure within the hemorrhoidal region, or to restore valvular competency.

An apparatus for performing the method of the invention comprises a catheter having a working end, means for heating a venous treatment area to cause shrinkage of the vein, wherein the means for heating is located at the working end of the catheter, and means for preventing further shrinkage after sufficient shrinkage of the vein, so that the vein continues to function.

In a more detailed aspect of a preferred embodiment of the invention, electrodes are employed for heating and shrinking the vein. The electrodes generate a radio frequency field around the circumference of the catheter in order to shrink the vein wall circumferentially and omnidirectionally when the catheter electrodes are positioned intraluminally within the vein. The field is controlled to maintain a specific temperature around the catheter in order to minimize coagulation within the vein, and to control the spread of heating within the venous tissue. The application and direction of RF energy to the venous tissue is capable of being controlled in order to achieve hemostasis in bleeding varices and minimize recurrence of bleeding.

A further aspect of a preferred embodiment is that the means for preventing further shrinkage include bowable members for controlling the outer diameter of the heating means to limit the amount of shrinkage. The bowable members that can be deflected radially outward for maintaining contact with the venous tissue. In an additional aspect of the preferred embodiment is that the bowable members are conductive so as to act as electrodes, and are substantially covered by an insulating film, except for the portion which is to come into apposition with the venous tissue. The bowable members further maintain the electrodes in apposition to the venous tissue to ensure that the heating effect is delivered towards the venous tissue, and not the blood moving through the vein.

These and other aspects and advantages of the present invention will become apparent from the following more detailed description, when taken in conjunction with the accompanying drawings which illustrate, by way of example, the preferred embodiments of the invention.

BRIEF DESCRIPTION OF THE DRAWINGS

FIG. 3 is a side view of an embodiment of a catheter having bowable electrodes in accordance with the invention coupled with a block diagram of a heat treatment system;

FIG. 4 is a partial side view of the working end of the catheter illustrated in FIG. 3, and having electrodes which deflect outwardly for increasing the effective diameter at the working end of the catheter in accordance with the present invention;

FIG. 5 is a cross-sectional view along lines 5—5 of the electrode for the catheter depicted in FIG. 4;

FIG. 6 is a cross-sectional view along lines 6—6 of FIG. 3, and depicts a catheter having four equidistantly spaced electrodes in accordance with the present invention;

FIG. 7 is a cross-sectional view of another embodiment of the catheter depicted in FIG. 6, this embodiment having four electrodes preferentially spaced to form two pairs of electrodes in accordance with the present invention;

FIG. 8 is a cross-sectional view of the catheter along lines 8—8 of FIG. 3;

FIG. 10 is a cross-sectional view along lines 10—10 of FIG. 9;

FIG. 11 is a partial cross-sectional side view of an embodiment of an over-the-wire balloon catheter having four equidistantly spaced apart electrodes on the surface of the balloon in accordance with the present invention;

FIG. 13 is a partial cross-sectional side view of another embodiment of the catheter having electrodes located within the balloon portion in accordance with the present invention;

FIG. 14 is a cross-sectional side view of another embodiment of the catheter having a bendable tip;

FIG. 15 is a side view of a deflection wire which can be used in conjunction with the catheter shown in FIG. 14 in accordance with the present invention;

FIG. 16 is a cross-sectional side view of the catheter of FIG. 14 in conjunction with the deflection wire of FIG. 15 in accordance with the present invention;

FIG. 17 is a cross-sectional side view of another embodiment of a catheter having a balloon on one side of the catheter and longitudinal electrodes on the other side of the catheter for moving the electrodes into appositional contact with the vein wall in accordance with the present invention.

FIG. 18 is cross-sectional top view of the embodiment of the catheter in FIG. 17 in accordance with the present invention;

DETAILED DESCRIPTION OF PREFERRED EMBODIMENTS

Figure 1:
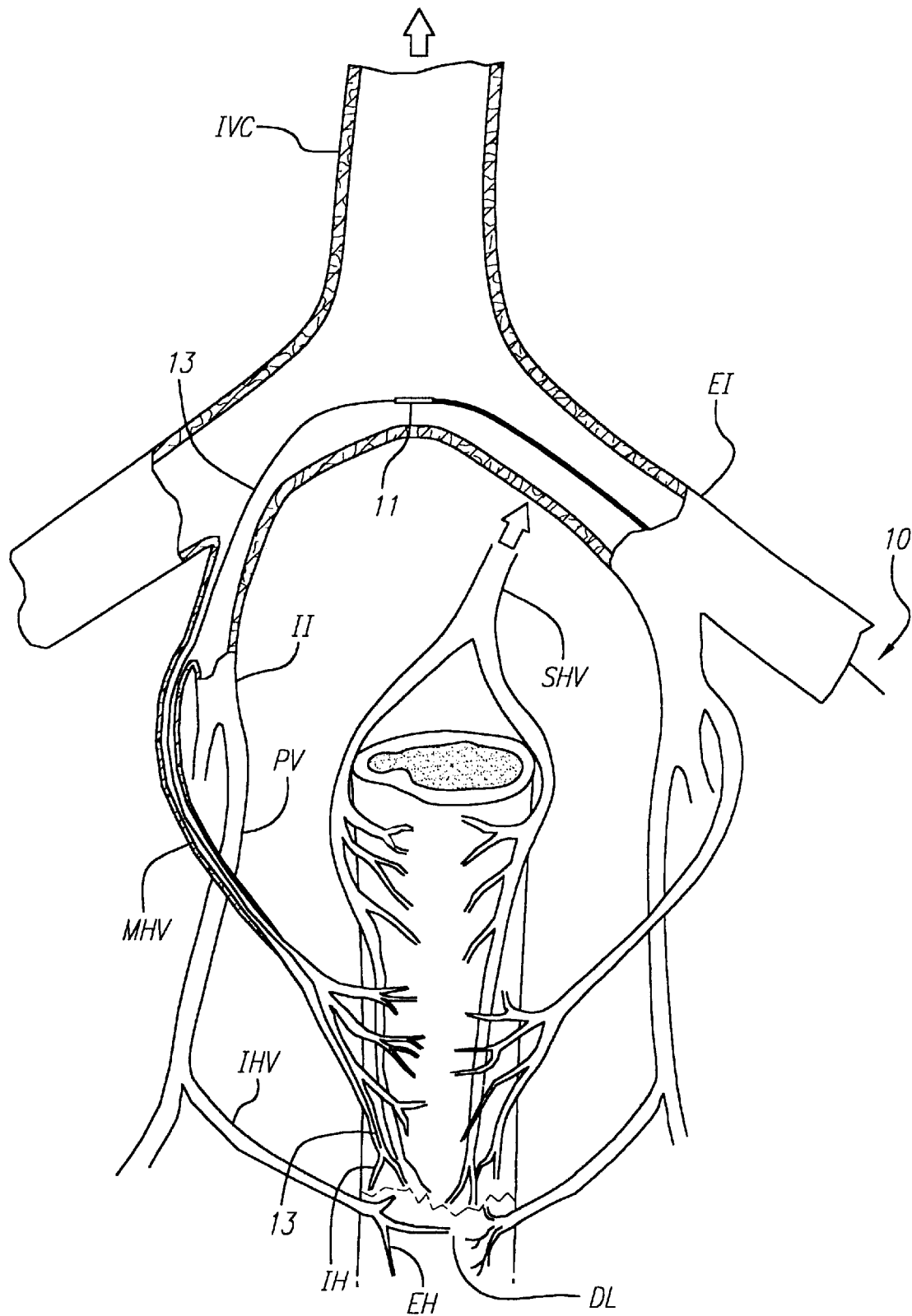
FIG. 1 shows a partial cross-sectional view of the venous system of the hemorrhoid region which is to be treated in accordance with the present invention.

As shown in the exemplary drawings, the invention is directed toward the intravenous treatment of veins using a catheter to deliver at least one electrode to a venous treatment site. As used herein, like reference numerals will designate similar elements in the various embodiments of the present invention to be discussed. In addition, unless otherwise noted, the term "working end" will refer to the direction toward the treatment site in the patient, and the term "connecting end" will refer to the direction away from the treatment site in the patient.

The method of the present invention for the minimally invasive treatment of venous insufficiency can be performed using a catheter to deliver at least one electrode at the working end of the catheter to a venous treatment site in order to restore the proper function of a vein leading to the hemorrhoidal region. An over-the-wire or rail wire guided catheter can be used to deliver the one or more electrodes through the tortuous bends in the venous system to the hemorrhoidal treatment site. The catheter can include a single RF electrode for monopolar heating where an external electrode having a large surface area is placed on the skin over the vein treatment site. In a bipolar arrangement, two or more RF electrodes can be situated at the working end of the catheter. The catheter and the electrodes can be configured for either arrangement. This and other embodiments of the catheter will be described in greater detail later. Particular discussion will be directed to the treatment of dilated veins in the hemorrhoidal region using RF energy, although the method of the present invention is well suited to treating veins in other areas of the body.

When treating the veins of the lower hemorrhoidal region, the access site is prepped and a percutaneous introducer is inserted into the vein. The procedure for the repair of incompetent veins can be accomplished by a qualified physician with fluoroscopic guidance, ultrasonic observation, or direct visualization. A guide wire is passed into the vein through the introducer, and advanced through to the venous treatment site. Alternatively, the catheter may be inserted into the vein directly and manipulated without a guide wire. The guide wire preferably has a spring wound tip. The guide wire is advanced retrograde to the venous treatment site, such as the most distal incompetent vein site which is to be repaired. Several intravenous paths may be taken to the hemorrhoidal treatment site.

A partial cross-sectional view of the venous system leading to the hemorrhoidal region is shown in FIG. 1. Hemorrhoids are generally defined as internal or external depending on whether they are formed above or below the dentate line DL, respectively. Internal hemorrhoids IH are commonly formed when the smaller veins draining to the superior hemorrhoidal vein SHV or the middle hemorrhoidal vein MHV become dilated. External hemorrhoids are commonly formed when the smaller veins draining to the inferior hemorrhoidal vein IHV become dilated.

One method of delivering the catheter 10 and guide wire 13 is to introduce the guide wire 13 into the external iliac vein EI on the side opposite to the dilated veins of the hemorrhoid. The guide wire is steered across the bifurcated branch of the inferior vena cava IVC to the inferior iliac vein II. The guide wire is then maneuvered into either the middle hemorrhoidal vein MHV to treat internal hemorrhoids, or the pudendal vein PV and then the inferior hemorrhoidal vein IHV to treat external hemorrhoids. The guide wire 13 is deployed and maneuvered into the middle hemorrhoidal vein MHV to treat an internal hemorrhoid. The guide wire 13 is maneuvered through the venous system until it reaches the dilated veins of the hemorrhoid. The catheter 10 is then delivered to the venous treatment site over the guide wire 13, as shown in FIG. 1. The working end 11 of the catheter 10 includes one or more electrodes for applying RF energy once properly positioned at the venous treatment site to cause shrinkage of the vein. The working end of the catheter further includes a flexible nose cone tip to allow tracking of the catheter over the guide wire and through bends in the venous vascular system. Fluoroscopy, x-ray, ultrasound, or a similar imaging technique could be used to direct the specific placement of the catheter and to confirm position within the vein. X-ray contrast material can be injected through or around the catheter to identify the incompetent venous sections to be repaired. This approach advantageously allows the guide wire or catheter to avoid sharp bends or turns while being steered to the venous treatment site. It is to be understood that other access sites can be used to treat either internal or external hemorrhoids.

Another method of delivering the catheter and guide wire is to introduce the guide wire into the superior hemorrhoidal vein and maneuver the guide wire through the superior hemorrhoidal vein SHV to the hemorrhoidal region. The guide wire is maneuvered into position, and the catheter is then delivered over the guide wire to the venous treatment site for the internal hemorrhoid. The venous treatment site is within the lumen of a dilated vein.

When the electrodes 12 of the catheter 10 are positioned at the venous treatment site, an RF generator is activated to provide suitable RF energy, preferably at a low power level, and, preferably at a selected frequency from a range of 250 kHz to 350 MHZ. For example, one suitable frequency is 510 kHz. One criterion for the selection of the applied frequency is to control the spread, including the depth, of the thermal effect in the tissue. Another criteria for the selection of the applied frequency is the capability of filtering circuits to eliminate RF noise from thermocouple signals.

The energy emitted from the electrodes is converted within the venous tissue into heat. As the temperature of the venous tissue increases, the venous tissue begins to shrink. The shrinkage is due in part to dehydration and the structural transfiguration of the collagen fibers in the vein. Although the collagen becomes compacted during this process, the vessel wall collagen still retains elasticity.

RF energy can be applied to heat the dilated venous section of a hemorrhoid. The dilated vein is shrunk to a normal or reduced diameter under the controlled application of RF energy which heats the venous tissue. Venous pressure on the lower venous sections of the hemorrhoid may be lessened, due to the decrease in the cross-sectional area of the vein. Valve competency in the lower venous sections may also be restored indirectly by the lessening of the venous pressure. Thickening of the vein will also occur during treatment, which can reduce the likelihood of the recurrence of vein dilation. The temperature and power of the RF energy may also be controlled to both shrink the hemorrhoid and cause the wall of the hemorrhoidal vein to become affixed to adjacent tissue.

Although applying RF energy can shrink the vein dilation near the formation of the hemorrhoid, extending the shrinkage to include higher venous sections can be advantageous in further lessening the effect of higher and increased venous pressure on the hemorrhoidal system. A contiguous axial section of dilated vein can be treated by applying RF energy along the dilated venous section, even if the section is extensive. For example, hemorrhoids are sensitive to pressures from the portal system, which can be transferred to the hemorrhoids through the superior hemorrhoidal vein SHV. Treatment of the superior hemorrhoidal vein by general shrinkage along an extensive section of the vein above the hemorrhoid can offset the dilating forces that arise from any increased pressures from the portal system. Such treatment may be desirable even if there is no significant dilation in the superior hemorrhoidal vein SHV.

Figure 2D:
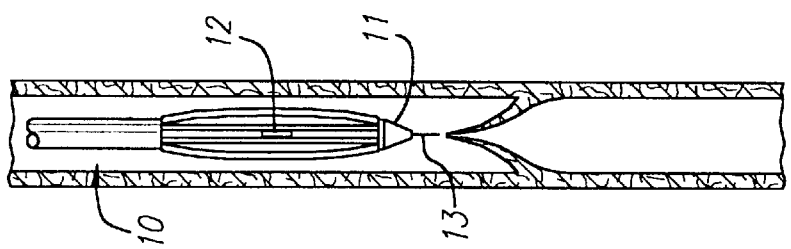
FIGS. 2a, 2b, 2c, and 2d are side views of an embodiment of a catheter treating a venous treatment site within a dilated vein in accordance with the present invention.
Figure 2C:
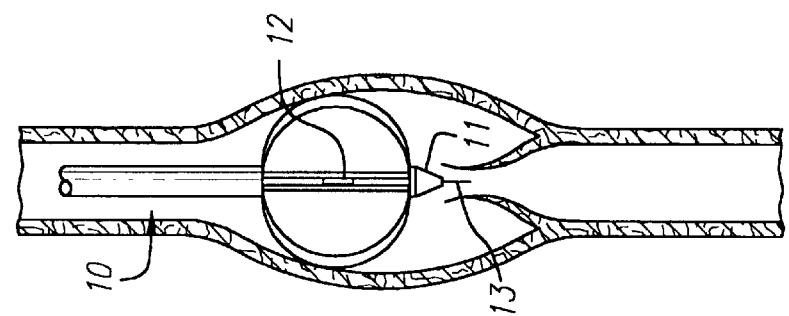
Figure 2B:
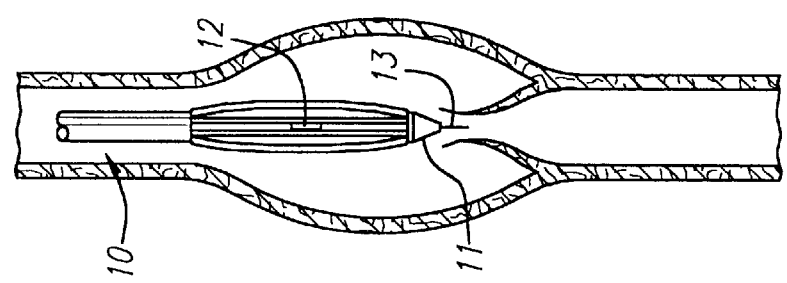
Figure 2A:
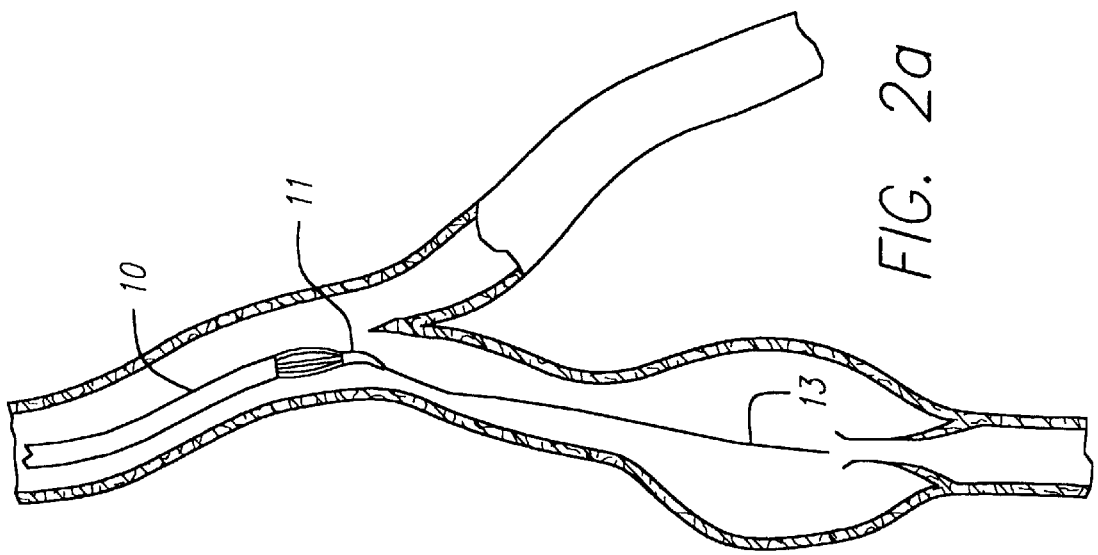

The catheter 10, as shown in FIG. 2a, is introduced over the guide wire 13 through the venous system. The tip 15 of the working end 11 of the catheter 10 is in the form of a nosecone which is flexible in order to travel over the guide wire and through bends in the venous system. As shown in FIG. 2b, the catheter 10 is delivered into the dilated venous section which may include an incompetent valve. The electrodes are then placed in apposition with the vein wall, preferably by mechanically bowing the electrodes 12 outwardly from the catheter 10 as shown in FIG. 2c. The application of RF energy from the electrodes causes the vein to shrink, and the effective diameter of the catheter, as defined by the bowed out electrodes, is mechanically decreased to control the amount of vein shrinkage. The bowed electrodes are held in position to define a specific effective diameter, as shown in FIG. 2d, to avoid occluding the vein. The catheter may be moved along the length of the dilated venous section to cause general shrinkage where the dilation is extensive.

RF energy is no longer applied from the electrodes after there has been sufficient shrinkage of the vein to alleviate the dilation of the vein. Substantial shrinkage may be achieved very rapidly, depending upon the specific treatment conditions, including the power level of the applied RF energy. The properties of the treatment site, such as temperature, can be monitored to provide feedback control for the RF energy. Other techniques such as impedance monitoring, and ultrasonic pulse echoing, can be utilized in an automated system which shuts down the application of RF energy from the electrodes to the venous section when sufficient shrinkage of the vein is detected and to avoid overheating or cauterization of the vein. Monitoring these values in an automatic feedback control system for the RF energy can also be used to control the power level and heating effect.

Sufficient shrinkage of the vein may be detected by fluoroscopy, venography, external ultrasound scanning, intravascular ultrasound scanning, impedance monitoring, temperature monitoring, direct visualization using an angioscope, or any other suitable method. For example, the catheter 10 can be configured to deliver an x-ray contrast medium to allow visualization by fluoroscopy for assessing the condition of the vein and the relationship of the catheter to the treatment area of the vein during the shrinkage process. As an alternative to fluoroscopy, external ultrasound techniques such as B-scanning using distinct ultrasound signals from different angles, or intravascular ultrasound can be used to acquire a more multidimensional view of the vein shrinkage at the treatment site, which improves the detection of uneven shrinkage in the vein. An angioscope may also be used to directly visualize and determine the extent and degree of vein shrinkage.

Where the catheter is designed with a fluid delivery lumen, a cooling fluid can be delivered through the delivery lumen to the bloodstream during RF heating of the vein being treated. The fluid may include radiodense contrast material. The delivered cooling fluid minimizes any heating effect on the blood, and reduces the risk of heating the blood to the point of coagulation. The fluid may be delivered through ports formed along the side of the catheter near the working end and the electrodes.

The working end 11 of the catheter 10 near the electrodes 12 can be used to physically limit the amount of shrinkage. The working end 11 is preferably sufficiently sized or enlarged to prevent the complete occlusion of the vein. Other schemes, such as an inflatable balloon, may be used to mechanically limit or control the amount of shrinkage in the vein or to displace blood from the treatment site. Such mechanical schemes can also be used to assure apposition between the electrodes and the venous tissue during treatment.

While providing for generalized shrinkage of the vein, the catheter may also be used to more directly treat the venous valves. The hemorrhoidal veins have bicuspid valves, and in a normal and competent valve, each cusp forms a sack or reservoir for blood which, under pressure, forces the surfaces of the cusps together to prevent retrograde flow of the blood and allow only antegrade flow to the heart. The arrows leading out the top of the inferior vena cava IVC and the superior hemorrhoidal vein SHV, as shown in FIG. 1, represent the antegrade flow of blood back to the heart. The venous valves prevent retrograde flow as blood is pushed forward through the vein lumen and back to the heart. In an incompetent valve, the cusps do not seal properly and retrograde flow of blood may occur. Incompetent valves may result from the stretching of dilated veins. As the valves fail, increased pressure is imposed on the lower veins and the lower valves of the vein, which in turn exacerbates the failure of these lower valves. Hemorrhoids may occur or become aggravated as a result. The valve cusps can experience some separation at the commissure due to the thinning and stretching of the vein wall at the cusps. When RF energy is applied within the dilated vein near the incompetent venous valve, shrinkage of the vein can restore valvular competency by reducing the dilation which is preventing the proper functioning of the venous valve.

In treating venous valves, the electrodes on the catheter are advanced until contact with the cusp of the venous valve is observed by fluoroscopy, ultrasound, or another detection method. The catheter is then pulled back slightly to allow treatment of the dilated section of vein. The electrodes are activated to deliver RF energy to the venous tissue and shrink the vein. The application of RF energy should be controlled to avoid unintentionally heating the valvular cusps. The shrinkage of the vein can be limited to prevent occlusion and allow the continued function of the vein. The outer diameter of the catheter or an extendable member can be controlled to limit the magnitude of the vein shrinkage.

After treatment, the commissure and the cusps of the venous valves should be closer together with little separation or prolapse, which indicates a restoration of the competency of the valve. Valvular competence may be determined by contrast injection or Doppler probe measurement. For example, a radiopaque contrast solution can be infused through the catheter lumen to assess valve competence via descending venography. It should be noted that reducing vein dilation by general shrinkage in a section above the section containing the incompetent venous valves could restore valvular competency by reducing the venous pressure on the valve and the dilation of the vein, which reduces the necessary span of the cusps. Also, direct placement of the electrodes across a vein valve can result in shrinkage of the loose, floppy leaflets, thereby preventing prolapse and reflux of blood through the valve.

Specific application of the RF energy to the venous valves can also be effective in restoring venous function and valvular competency. The catheter 10 can be configured to position the electrodes within the vein valve segment and to appose the electrodes with the venous section to be repaired. The catheter is capable of being deflected, torqued, or otherwise moved to allow for proper placement of the electrode. The catheter can be manufactured to provide a controllable bend near the working end. For example, the bend may be formed from a shape-memory metal, manipulatable by a system of wires, a torquable braid, or a permanent bend in the catheter. Manipulating the working end of the catheter enables preferential heating along the vein wall being treated, if desired, where the electrodes are placed closer to one side of the vein wall.

The catheter 10 can be repositioned within the vein so as to treat as many venous sections and valves as necessary. RF energy is applied to each venous section to be repaired, until all of the desired venous sections are repaired and the valves are rendered competent. Multiple incompetent valves and dilated venous sections may be treated and repaired in a single minimally invasive procedure. If desired, a second introducer can be inserted into the patient in order to treat incompetent venous sections in the other vein systems, such as the superior hemorrhoidal vein.

One embodiment of the catheter 10 having electrodes 12 on the working end 11 which causes localized heating of the surrounding venous tissue and shrinkage of the vein is shown in FIG. 3. The catheter 10 includes electrodes 12 in the form of four conductive elongate members which can be bowed outward. The bowable electrodes are formed along the circumference of the catheter, but are not fixed to the catheter. The catheter itself is fit through a suitably sized sheath for the procedure. For example, a 7 French sheath, which has about a 2.3 millimeter (mm) diameter, may be used. The sheath is composed of a biocompatible material with a low coefficient of friction. The working end 11 of the catheter includes a tip 15 which is attached to one end of each electrode, and the other end of each electrode is connected to a sliding sleeve 36 formed along the exterior of the catheter shaft. The outer sleeve extends down the length of the catheter to allow the physician to directly and mechanically control the effective electrode diameter during the application of RF energy. As the the slidable sleeve 36 is moved towards and away from the working end in response to a control actuator 33, the electrodes 12 are urged radially outwards and inwards, respectively. The tip 15 essentially remains stationary while the slidable sleeve is moved. Moving the sleeve 36 back toward the connecting end of the catheter pulls back and flattens the electrodes against the catheter before insertion or withdrawal from the vein. Moving the sleeve 36 forward toward the working end of the catheter causes the electrodes to deflect and radially bow outward to an increased diameter. The contact area of the electrodes is bowed outwardly as the opposite ends of the longitudinal electrode are moved closer together. The outer sleeve may be moved a preset distance to cause the electrodes to bow outwardly to a known diameter. Bowing the electrodes outwardly also places the electrodes in apposition with the venous tissue to be treated. By manipulating the slidable sleeve to adjust the effective diameter of the catheter defined by the radial bowing of the electrodes, contact between the electrodes and the vein wall can be maintained as the vein shrinks. The control actuator 33 is a switch, lever, threaded control knob, or any other suitable mechanism, preferably one which can provide fine control over the movement of the slidable sleeve. By using the control actuator to move the slidable sleeve, the effective diameter of the electrode can be controlled for treating vein lumen having different diameters, and for providing varying degrees of vein shrinkage.

The tip 15 has a nosecone shape, or can have any shape which allows tracking of the catheter over the guide wire and through bends in the venous vascular system. The nosecone tip can be fabricated from a polymer having a soft durometer, such as 70 Shore A. Alternatively, the nosecone can be constructed from a spring covered with a thin layer of polyethylene shrink tubing.

The extent of shrinkage is controlled by the effective diameter of the catheter and the electrode combination. The electrodes 12 are bowed radially outward as part of the effective diameter of the catheter so as to come into apposition with the vein wall. After being placed in contact with the venous tissue, and the effective diameter could be mechanically reduced to control shrinkage while RF energy was being applied. The electrodes 12 are preferably operated as bipolar electrodes. As RF energy is applied to the electrodes, an RF field is created around the effective diameter of the catheter as defined by the bowed electrodes, and the vein becomes heated and begins to shrink. The effective diameter of the catheter is reduced under the control of the physician to control the amount of shrinkage. As the effective diameter is decreased, the electrodes continue to maintain apposition with the venous tissue. The extent of vein shrinkage is monitored by fluoroscopy, or any other suitable method. After shrinking the vein to the desired diameter, the application of RF energy from the electrodes 12 is ceased. The desired diameter of the vein is the final effective diameter of the catheter, as defined by the deflected electrodes 12.

The electrodes 12 have an elongated shape and may be fabricated from stainless steel, spring steel, or nitinol, so that the electrodes 12 would be biased to return to a reduced diameter profile. The electrodes are rounded wires to facilitate flexing of the catheter at the working end while being delivered through the bands of tenuous venous vasculature. The diameter of the electrodes are preferably between about 0.005 to 0.015 inches (about 0.12 to 0.35 mm), but can be up to about 0.03 inches (about 0.7 mm). Other shapes including rectangular wires having relatively large flat surfaces for contacting the vein wall can be used. Such rectangular wires can have widths ranging from 0.005 to 0.05 inches, and preferably between 0.015 and 0.030 inches, to allow four to eight electrodes around the catheter shaft.

The entire length of the bowable longitudinal electrode is conductive, and insulation 35 is provided over the majority of the electrode surface, as shown in FIGS. 4 and 5, in order to prevent any unintended heating effects. Only a modest portion of the conductive surface is exposed to act as the electrode. The heating effect is greatest when the electrodes are close together since the electrical field density (power density) is greatest at this point. The ends of the electrodes are insulated from each other to prevent creating electrical field densities that are larger at the ends compared to that around the middle of the electrode. As the effective diameter increases, greater field disparities between the ends and the outwardly bowed midsections could be created if no insulation were provided. The insulation 35 can be polyimide, paralyene, or another type of insulating material. The insulation 35 provided along the sides and the back of the electrodes opposite from the vein wall further prevents heating of the blood flowing in the vein, which should also reduce the likelihood of coagulation. Where the wire has a rectangular shape, then the exposed area which functionally acts as the electrode would then occupy only one face of that wire. As shown in FIG. 5, the insulation 35 surrounding the electrode can further cover the peripheral edges of the exposed face of the electrode to further isolate the blood flow from unintended heating effects.

The exposed area of the electrode is preferably the area which directly contacts the vein wall during apposition. The heating effect is then focused into the vein wall. The exposed surface area of the electrode should be as great as allowable while maintaining a consistent distance between the exposed sections of the electrode along the circumference of the effective diameter. The larger the exposed surface of the electrodes apposed against the vein wall during shrinkage, the greater the surface area of the vein wall affected by the electric field generated by the electrodes. The exposed area for the electrode can be substantially flat to enhance uniform contact with the vein wall and for controlling the diameter of the vein.

A sensor 30 such as a small thermocouple for measuring temperature is attached to the electrode 12. As shown in the cross-sectional view of FIG. 5, the temperature sensor 30 is soldered in place through a hole in the electrode so that the sensor is nearly or substantially flush with the exposed surface of the electrode. The sensor can accurately sense the temperature of the vein wall in apposition with the exposed electrode surface. The leads to the sensor are situated on the opposite side of the electrode which is insulated.

A cross-sectional view of the electrodes 12 of FIG. 3 along lines 6—6 is shown in FIG. 6. In the four-electrode configuration, a preferred embodiment is to have the electrodes 12 spaced equidistantly apart along the circumference of the catheter. Although the catheter has been described as having a four electrode configuration, it is to be understood that the catheter may include a different number of electrodes, for example, six, eight, or more bowable electrodes, in order to lessen the inter-electrode gap and reduce the amount of power required to heat the venous tissue. The polarity of each electrode is preferably opposite to the polarity of the immediately adjacent electrodes to provide for omnidirectional and circumferential shrinkage of the vein. Thus, a relatively uniform RF field would be created along the circumference of the catheter by the alternating electrodes. In another embodiment, as shown in FIG. 7, if adjacent electrodes were to be moved closer together, two effective pairs of active electrodes of opposite polarity would be formed along the circumference of the catheter. While an RF field would still be formed along the entire circumference of the catheter, the RF field would be strongest between the closest adjacent electrodes of opposite polarity. Shrinkage of the vein would be concentrated where the RF field was strongest.

It is to be understood that although a bipolar arrangement is described, a monopolar arrangement may also be used. In a monopolar arrangement, an inside electrode, such as a mesh or wire electrode, is inserted into a patient's body. An outer electrode having a much larger surface area than the inside electrode is placed on the outer surface of the patient's body near the treatment site. For example, an external metal plate is placed on the skin over the region to be treated by the inside electrode. The electrodes are connected to an RF generator which produces an electric field within the patient's body. Because the surface area of the inner electrode is much smaller than that of the outer electrode, the density of the electric field is much higher around the inside electrode. The electric field reaches its highest density between the two electrodes in the region near the inside electrode. The increased density of the field around the inside electrode allows localized heating of the tissues surrounding the inside electrode. The degree of heating may be dependent on such factors as the impedance and dielectric constant of the tissue being heated.

The working end of the catheter further includes a guide wire lumen 38 for accepting the guide wire 13. The tip of the guide wire 13 is preferably rounded. The guide wire lumen 38 is preferably insulated so as to prevent or minimize any coupling effect the electrodes 12 may have on the guide wire 13. The guide wire can be removed before the application of RF energy to the electrodes. A cross-sectional view of the catheter 10 taken along lines 8—8 FIG. 3 is shown in FIG. 8. The guide wire 13 is shown centrally located within a guide wire lumen 38. The guide wire lumen 38 is surrounded by a layer of insulation material 22, which in turn is surrounded by a copper braid 24 for stability and stiffness, as well as for providing flexible torqueability to the catheter. An insulation sheath 26 covers the copper braid 24, and contains the conductive leads 20 to the electrodes as well. In a bipolar arrangement, the conductive leads 20 have opposing polarity. In an over-the-rail type catheter, the guide wire is outside the catheter until arriving at the working end of the catheter, upon which, the guide wire enters the guide wire lumen. The guide wire lumen 38 is preferably located within the insulation material 22 in order to electrically isolate the guide wire 13 from the electrodes 12. The guide wire lumen can also allow for the delivery or perfusion of medicant and cooling solution to the treatment area during application of the RF energy.

The bowable electrodes 12 are preferably located between the sensors 30, as shown in FIG. 4, for measuring values such as impedance. In measuring impedance, as will be described in further detail later, the area between the electrodes often provides the most relevant data. It is to be understood that the sensors 30 may be used to measure other values including temperature and ultrasound signals. Further, the positioning of the sensors 30 on the catheter 10 may be varied depending on the value being measured. For example, when measuring temperature, it may be desirable to place the sensor on or immediately adjacent the electrode. The temperature sensor senses the temperature of the tissue around the electrodes. When measuring echo signals of pulsed ultrasound, the sensors may be placed between the electrodes, or at the tip of the catheter. When measuring pulse echo ultrasound signals, the catheter is preferably rotated to resolve an image of the environment surrounding the catheter and the sensors.

The sensors 30 measure parameters used to determine the extent of vein shrinkage. For example, the sensors can be temperature sensors such as thermocouples. The temperature sensors may be included on the catheter near or on the electrodes on the working end, as shown in FIG. 5, to monitor the temperature surrounding the electrodes and the venous section being treated. Application of RF energy from the electrodes may be halted when the monitored temperature reaches or exceeds the specific temperature at which venous tissue begins to shrink. The signals from the temperature sensors are input to the microprocessor 32 for controlling the application of RF energy to the electrodes in accordance with the monitored temperature.

In another embodiment, the sensors 30 can be sensing electrodes which measure the impedance of the venous tissue in contact between the electrodes 12. The configuration of the sensors on opposite sides of the electrodes 12, as shown in FIG. 4, can be used to measure impedance. A constant RF current is emitted from the electrodes 12, and the impedance may be measured between the electrodes directly. The voltage across the electrodes is measured by the sensing electrodes to detect the impedance of the volume between the electrodes. The voltage measured is proportional to the impedance Z between the electrodes, where $Z=V/I$ and the current, I, is constant. The impedance changes as a function of the diameter of the vein because there is less blood and less conductance as the venous diameter decreases. As the volume decreases due to shrinkage, the amount of conductive volume between the electrodes decreases, and the increased impedance causes a corresponding increase in the measured voltage. This technique allows for the measurement of vein shrinkage in relative terms. The signals from the sensing electrodes are input to a monitor, or microprocessor 32 which could send control signals to the RF generator 34 in order to control the application of RF energy to the electrodes in accordance with the relative impedance measured. Alternatively, the signals from the sensing electrodes are displayed visually on a monitor in order to allow for manual control by the physician. Measurements of the applied current and voltage applied to the electrodes can also be used to arrive at the impedance of the treatment site.

Instead of sensing electrodes or thermocouples, another embodiment includes ultrasonic piezoelectric elements which emit pulsed ultrasound waves as the sensors. The piezoelectric elements are operated in a pulse-echo manner to measure the distance to the vein wall from the catheter shaft. Again, the signals representative of the pulse-echo would be input to the microprocessor 32, or to a monitor to allow for manual control, and the application of RF energy would be controlled in accordance with the distance computed between the catheter and the vein wall.

Figure 9:
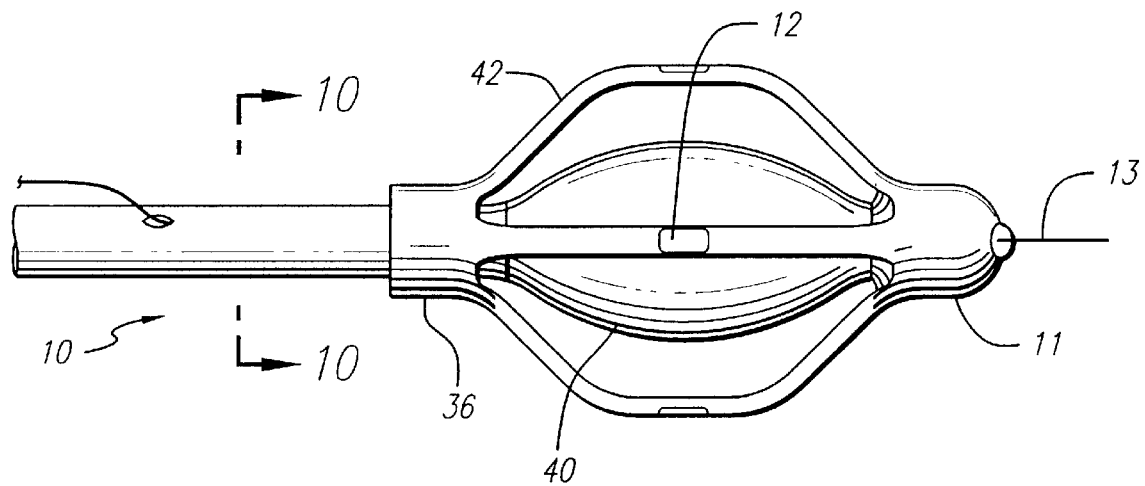
FIG. 9 is a partial side view of the working end of another embodiment of a catheter having a balloon and bendable members with electrodes in accordance with the present invention.

Another embodiment of the catheter 10, as shown in FIG. 9, includes bowable elongate members 42 having one end anchored to the working end 11 of the catheter, and the other end slidably connected to the catheter towards the connecting end. The catheter shown in FIG. 9 is similar to that shown in FIG. 3, except that instead of having the elongate members act as the electrodes themselves, the electrodes 12 are located on the elongate members 42. The elongate members 42 preferably include a flat central area for the electrodes 12. The central area remains substantially flat as the elongate members 42 are deflected and bowed outwardly. The substantially flat central area allows for a more uniform contact with the vein wall. The flat area establishes a larger surface area to assure contact between the electrode 12 on the elongate member and the vein wall. It is to be understood that the flat area need not be centrally located on the elongate member 42. The flat area should be located so as to be the first area that contacts the vein wall. The elongate members 42 at the working end of the catheter are connected to a movable tip manually controlled by a diameter actuator located at the connecting end of the catheter. The movable tip 17 is connected to the diameter actuator by an actuation wire 37 running centrally through the catheter. The diameter actuator may be threaded onto the connecting end of the catheter. Maneuvering the diameter actuator into and out of the connecting end of the catheter causes a corresponding movement in the movable tip at the working end of the catheter via the actuation wire. If the movable tip 17 is pulled toward the connecting end by the diameter actuator, then the electrodes 12 are bowed outwardly. The bowed electrodes 12 preferably expand out to treat veins having diameters of up to ten mm or more. If the movable tip 17 is pushed forward by the actuator wire 37, the electrodes 12 are then retracted towards the shaft of the catheter. Contact between the electrode and the vein wall can be maintained with the vein wall as the vein shrinks.

In one embodiment, the balloon 40 is located between the catheter shaft and the elongate members 42. Manual manipulation of a sliding sleeve or a movable tip is not required in this embodiment, and the sliding sleeve, if used, need not travel any substantial length of the catheter. The balloon 40 may be either an elastic, such as latex, or noncompliant material. The balloon 40 is inflated and comes into contact with the elongate members 42. As the balloon 40 is further inflated, the electrodes 12 are moved outwardly in a radial direction as the elongate members are deflected and bowed by the expanding balloon 40. The balloon is preferably inflated using a non-conductive fluid, especially where the elongate members contain the electrodes, or where the elongate member itself is conductive so as to act as the electrode. When the proper diameter for the electrodes is reached, the inflation of the balloon ceases, and the application of the RF energy begins.

The balloon 40 covers a large surface area over the venous treatment site, and ensures proper electrode placement relative to the vein wall while controlling the amount of venous shrinkage. More precise control over the shape and diameter of the balloon is possible using the bowable members. The balloon can also be used to control the effective diameter of the catheter at the working end. As RF energy is applied, the vein begins to shrink down to the effective diameter of the catheter. The effective diameter of the catheter is reduced under the control of the physician to control the amount of shrinkage. As the effective diameter is decreased, the electrodes continue to maintain apposition with the venous tissue. The application of RF energy from the electrodes 12 is terminated after shrinking the vein to the desired diameter, which is the final effective diameter as defined by the diameter of the balloon 40 and the deflected elongate members 42. The balloon 40 is then deflated to a minimal profile to allow movement of the working end of the catheter. The elongate members 42 are preferably fabricated from spring steel or nitinol so that the elongate members 42 would be biased to return to a reduced diameter profile when the balloon is deflated.

In another embodiment, the ends of the elongate members are instead slidably located within longitudinal slots or channels disposed along the circumference of the catheter. The ends of the bowable members would slide towards the working end within these channels as the members are deflected or bowed outwardly, and retreat back towards the connecting end in order to return to their original configuration. A mechanism such as a push rod can be included to prevent movement of the members in the channels, and limit radial contraction of the electrodes at a specific effective diameter.

In another alternate embodiment, the electrodes and the elongate members could be replaced by a single wire mesh or braided electrode, preferably when applying RF energy in a monopolar configuration. As before, the balloon could radially extend the mesh electrode outward into apposition with the vein wall. The balloon further controls the amount of vein shrinkage.

An alternative method for changing the effective diameter of the catheter is to move or deflect the electrodes into direct contact with the vein wall and then allow the vein wall to alter the effective diameter. As the electrodes emit RF energy, the vein wall shrinks and pushes the electrodes inwardly towards the catheter. The vein shrinkage reduces the effective diameter directly, rather than by the active control of the physician, thereby eliminating the need for constant fine mechanical adjustments to the effective diameter. A mechanism such as a push rod or fixed-diameter balloon may be included to prevent further radial contraction of the electrodes at a specific effective diameter, thereby controlling and limiting the amount of vein shrinkage. This has the advantage of maintaining the electrodes in apposition with the venous tissue so that the tissue is heated more than the surrounding blood, without requiring the physician to adjust the effective diameter of the catheter while applying the RF energy.

Other devices which are controllably expandable or extendable may be used to limit the shrinkage of the vein to a desired size. For example, a bowable conductive deflection wire may be located on one side of the catheter for achieving apposition with the vein wall. Furthermore, the nonexpandable catheter shaft and electrode shown in FIG. 3 may be used to limit the amount of vein shrinkage during the procedure, so that the vein shrinks down to the fixed diameter of the catheter.

Figure 12:
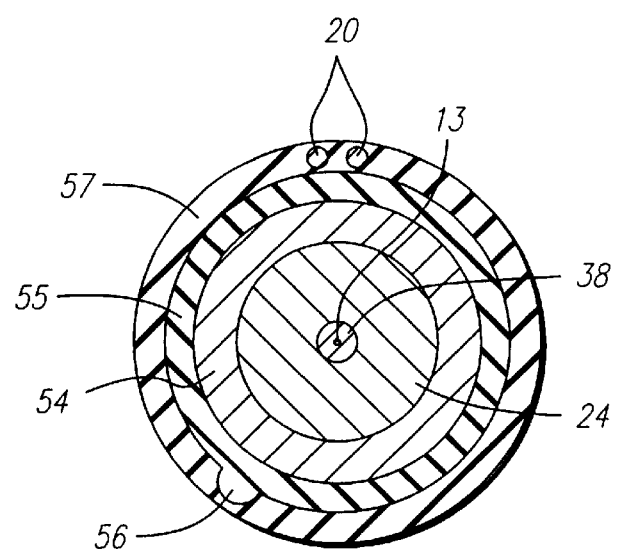
FIG. 12 is a cross-sectional view taken along the lines 12—12 of the over-the-wire balloon catheter in FIG. 11.

A balloon expandable embodiment, as shown in FIG. 11, includes the four longitudinal electrodes 12 arranged in longitudinal fashion around the circumference of the balloon 40 of the catheter 10. The electrodes may be located either on the inside or outside surface of the balloon. This embodiment is similar to the embodiments disclosed and described in connection with FIGS. 3 through 10. The particular positioning and orientation of the longitudinal electrodes is preferably equidistant so as to provide omnidirectional shrinkage and minimize lengthwise contraction of the vein. Other electrode configurations may also be employed along the balloon, including having only one pair of electrodes on one side of the balloon to focus the heating effect on that one side. The catheter 10 as shown in FIG. 12 is an over-the-wire type in which the catheter travels over a guide wire 13 through a guide wire lumen 38. The catheter 10 further includes the braided shield 24 surrounding the guide wire lumen 38. A braid tube 54 is formed around the braid 24. The lumen 56 for the balloon 40, and the balloon tube 55, encircle the braid tube 54. The braid tube forms a sealing barrier against the inflation fluid leaking into the guide wire lumen 38 from the balloon lumen. The exterior of the catheter includes a retainer tube 57 holding the conductor leads 20, which connect the electrodes 12 to the RF generator. A cross-section of the shaft of the catheter 10 along lines 12—12 of FIG. 11 is shown in FIG. 12.

In another embodiment, the electrodes 12 are located under the balloon 40 of the catheter 10. This embodiment, which is shown in FIG. 13, allows for conductive heating of the venous tissue. The catheter 10 shown in FIG. 13 is an over-the-wire type in which the catheter completely travels over the previously introduced guide wire 42. The balloon is inflated and expands to come into contact with the venous tissue. As discussed previously, the inflated balloon 40 is used to control or limit the magnitude of shrinkage of the vein to the outer diameter of the inflated balloon 40. The effective diameter is controlled by the selective inflation and deflation of the balloon 40. The inflation medium of the balloon 40 is preferably a conductive fluid, such as saline solution, so that a significant amount of the RF energy will still be transferred to the surrounding venous tissue. However, the inflation medium may absorb a certain amount of the RF energy, which will then be converted to heat. This diffusion of the RF energy could provide greater control over the shrinkage of the vein. Alternatively, a conventional heater coil or curie point element could be used in place of the electrodes 12 in order to directly heat the inflation medium, which in turn would conductively transfer the heat to the venous tissue.

An embodiment of the catheter 10 capable of being deflected by a shaft deflection wire 29 is shown in FIGS. 14, 15, and 16. By deflecting the working end of the catheter, selective apposition between the electrodes at the working end and the venous tissue at the treatment site can be maintained. The catheter 10, which is shown in FIG. 14, includes a silver-coated copper shield 24 and an outer layer of insulation 26. The electrodes 12 may be four circumferentially spaced longitudinal electrodes, as previously discussed. FIGS. 14 and 16 only show two of four longitudinal electrodes. The catheter 10 further includes a stiffening jacket 25 formed around the catheter shaft, except for the working end of the catheter. A central hollow wire lumen 27 extends through the length of the catheter. The shaft deflection wire 29 has a stiff bend formed near its working end, as shown in FIG. 15. The deflection wire is pushed through the wire lumen 27 of the catheter 10, as shown in FIG. 16. The portion of the wire 29 beyond the stiff bend of the wire, and which advances through to the tip of the working end of the catheter, is preferably flexible and pliant. The stiffening jacket 25 prevents the catheter shaft from being deflected by the shaft deflection wire 29 until the stiff bend of the deflection wire reaches the working end of the catheter. The stiff bend in the deflection wire 29 moves the working end 11 of the catheter to one side. Alternatively, the deflection wire 29 is a shape-memory metal which would be relatively straight until actuated to form a bend. The electrodes 12 may then be selectively placed in apposition with the specific venous tissue to be treated by rotating the catheter shaft as desired. A contrast medium may also be administered to the treatment site through the lumen 27. Further, a cooling solution or fluid may be delivered to the treatment site through the lumen 27. The lumen further includes side ports 28 formed at the working end near the electrodes 12 for delivering the contrast medium and the cooling fluid. Alternatively, the lumen 27 could be closed at the tip of the working end of the catheter in order to allow an injection of contrast media or cooling solution to be forced out the side ports 28. Closing the lumen 27 at the tip further allows the deflection wire 29 to be made more stiff without concern for the stiffer wire extending past the catheter.

Another embodiment uses an asymmetrical balloon 40 to deflect the electrodes 12 at the working end 11 of the catheter to one side. The electrodes 12 are a pair of longitudinal electrodes located on one side of the catheter. As shown in FIGS. 17 and 18, the balloon 40 is located on the opposite side of the catheter. When the balloon 40 is inflated, the opposite side of the working end 11 accommodating the longitudinal electrodes is moved into apposition with the venous tissue to be treated. After treating the dilated venous section, the balloon 40 is deflated, and the catheter removed from the vasculature. It should be noted that the other mechanisms for deflecting the working end of the catheter may be used. The catheter further includes the jacket 26, the braid 24, and the insulation 22.

Figure 19:
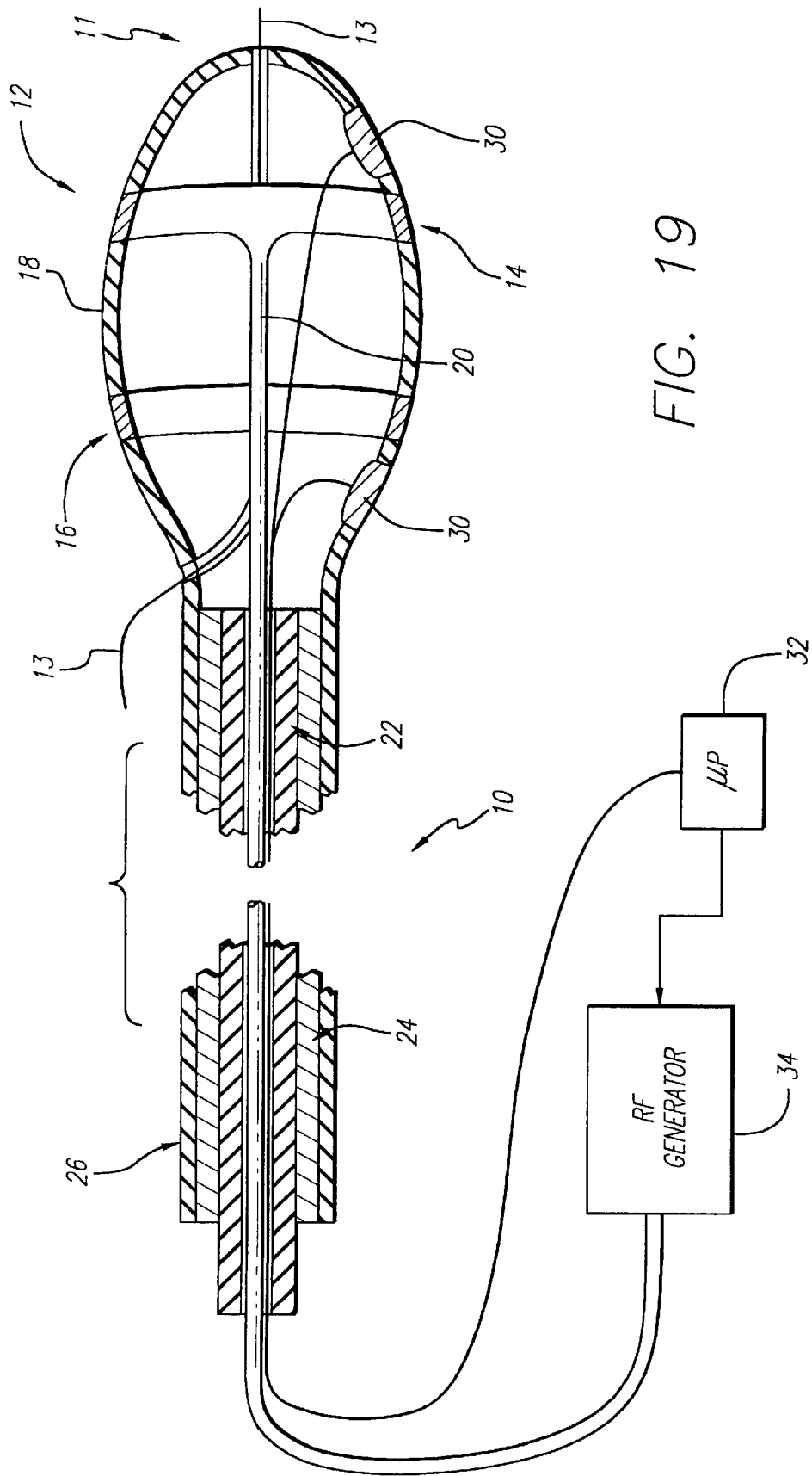
FIG. 19 is a partial cross-sectional side view of an embodiment of a catheter having a bulbous tip and ring electrodes for treating a dilated vein in accordance with the present invention coupled with a block diagram of a heat treatment system.

Another embodiment of the catheter 10 having electrodes 12 on the working end 11 which causes localized heating of the surrounding venous tissue and shrinkage of the vein is shown in FIG. 19. The electrodes 12 include two ring electrodes 14 and 16. The end ring electrode 14 acts as the active electrode, and the ring electrode 16 acts as the return electrode, or vice versa. The working end of the catheter includes a lumen for accepting the guide wire in an over-the rail type delivery system. The tip of the guide wire 13 is preferably rounded. The lumen is preferably insulated so as to prevent or minimize any coupling effect the RF electrodes may have on the guide wire.

The end ring electrode 14 is preferably spaced away from the tip of the working end of the catheter which may be formed from plastic or some other non-conductive material. The RF field created by the ring electrodes 14 and 16 should not extend past the end of the catheter. The inert non-conductive tip of the working end of the catheter helps prevent shrinkage past the end of the catheter by limiting the extent and formation of the RF field. This non-conductive tip acts as a shrink-limiting mandrel to prevent the veins from shrinkage to a diameter less than the catheter tip and may extend 2 to 25 mm past the electrode 14. Both electrodes 14 and 16 are preferably made from stainless steel. An insulator material 18 is located between the end electrode and the ring electrode. The catheter 10 and electrodes 12 should be constructed from materials which would allow visualization under fluoroscopy, x-ray, ultrasound, or other imaging techniques. For example, the catheter 10 may be configured to deliver x-ray contrast medium to allow visualization by fluoroscopy. Contrast media injected into the vein may be used to assess the condition of the vein and the relationship of the catheter to the treatment area of the vein by phlebography during the shrinkage process.

The catheter 10 includes a stranded, twisted center conductor 20 surrounded by a layer of insulation 22. A silver-coated copper braid 24 surrounds the insulated center conductor, and provides flexible and torquable characteristics to the catheter shaft. A sheath 26 covers the copper braid 24. The sheath 26 is preferably made of an electrically resistive, biocompatible material with a low coefficient of friction. The center conductor 20 is connected to a power source 34 such as an RF generator, to provide RF energy to the electrodes 12.

Figure 20:
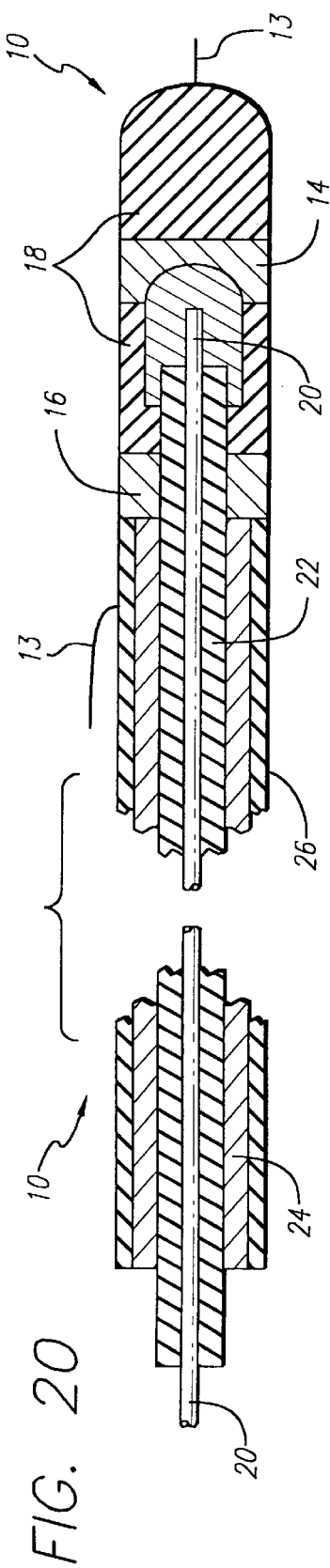
FIG. 20 is a partial cross-sectional side view of an embodiment of a catheter having a flush tip at the working end and ring electrodes for treating a dilated vein in accordance with the present invention.

The working end 11 of the catheter 10, as shown in FIG. 19, is rounded to provide an atraumatic tip. The working end 11 of the catheter 10 has an enlarged dimension which limits the amount of local vein shrinkage. An enlarged atraumatic tip may be achieved using a bulbous shape for the working end 11. Alternatively, the working end 11 and the ring electrodes 14 and 16 are flush with the shaft of the catheter as shown in FIG. 20. Different sized working ends 11 and electrodes 12 may be manufactured separately from the catheter 10 for later assembly with the shaft of the catheter 10 so that a single catheter shaft may be used with working ends having a variety of diameters. A working end having a specific size or shape could then be used with the catheter 10 depending on the type of vein being treated. Catheters need not be sized for the smaller veins and venues if only general shrinkage of the larger sections of the vein are to be performed to reduce the venous pressure. For example, certain larger veins have a diameter of seven to eight mm, while other veins only have a diameter of 2 to 3.5 mm. Other methods, such as monitoring the amount of shrinkage by fluoroscopy, may be used to determine and control the amount of shrinkage. In other respects, the construction of the catheter in FIG. 20 is similar to that of FIG. 19, as previously discussed.

Figure 21:
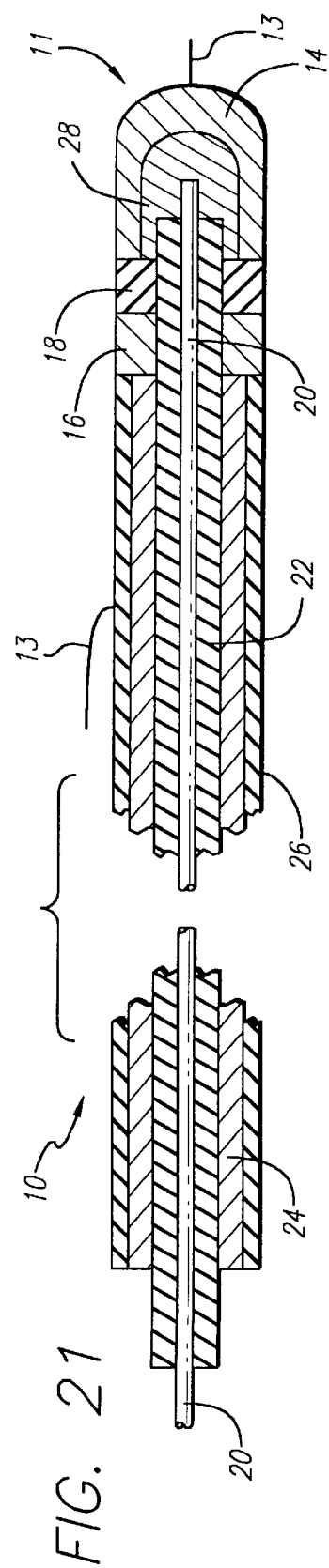
FIG. 21 is a partial cross-sectional side view of an embodiment of a catheter having a cap electrode for treating a dilated vein in accordance with the present invention.

Another embodiment of the catheter 10 includes an end electrode 14 which is a cap electrode formed on the tip of the working end 11 of the catheter 10, as shown in FIG. 21. The end electrode 14 is preferably fabricated from stainless steel. The cap electrode 14 acts as the active electrode, and the ring electrode 16 acts as the return electrode. Although described as a bipolar arrangement, the catheter may include only a single cap electrode in a monopolar arrangement. The cap electrode 14 of the catheter 10 is rounded to provide an atraumatic tip so as to minimize any damage to the surrounding venous tissue as the catheter is manipulated through the vein. The electrodes and the working end, as shown in the exemplary FIG. 21, are substantially flush with the remainder of the catheter. Alternatively, the cap electrode and the working end 11 of the catheter 10 may have an enlarged dimension from the remainder of the catheter. The braid sheath 26 covers the silver-coated, copper braid 24 of the catheter, and the sheath is flush with the outer diameter of the ring electrode 16. An insulator tube 18 is located between the end electrode and the ring electrode. At the working end of the catheter, a solder fill is formed between the center conductor 20 and the end electrode 14. The center conductor 20 is isolated from the ring electrode 16 by the insulation 22. The guide wire 13 is preferably insulated from the cap electrode 14.

Figure 22:
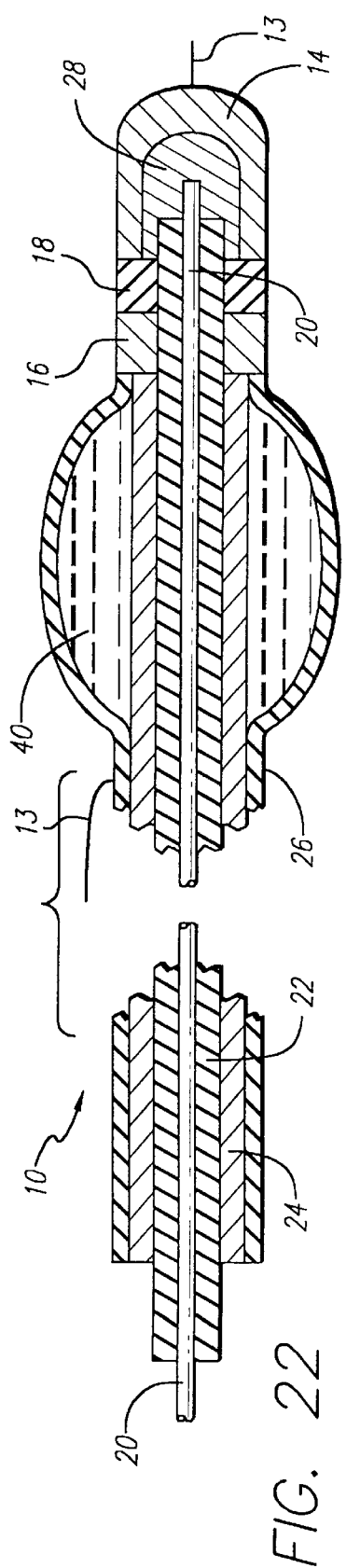
FIG. 22 is a partial cross-sectional view of another embodiment of a catheter having a cap electrode and a balloon to center the electrode within the vein to be treated.

In another embodiment, an inflatable balloon 40 coaxially placed over the braided shaft centers the catheter 10 and the electrodes 14 and 16 within the vein lumen in order to avoid unintended electrode contact with the vein lumen which could otherwise result in uneven heating of portions of the vein lumen. The balloon 40 is located adjacent the electrode 16, as shown in FIG. 22, which is closer to the connecting end of the catheter. The balloon 40 is preferably expandable and compliant, and fabricated from an elastic material such as latex, to provide intermediate diameters. The balloon is inflated with dilute radiopaque contrast for fluoroscopic visualization.

As can be readily ascertained from the disclosure herein, the procedure of the present invention is accomplished without the need for prolonged hospitalization or postoperative recovery. Early treatment of venous disease could prevent more serious complications, and the cost of treating venous diseases would be significantly reduced. Furthermore, the minimally invasive nature of the disclosed methods would allow the medical practitioner to repair or treat several venous sections in a single procedure in a relatively short period of time.

It is to be understood that the type and dimensions of the catheter and electrodes may be selected according to the size of the vein to be treated. Furthermore, although described as using RF energy from the electrode, it is to be understood that other forms of energy such as microwaves, ultrasound, direct current, circulating or non-flowing heated fluid, radiant light, and lasers may be used, and that the thermal energy generated from a resistive coil or curie point element may be used as well. In addition, although the present invention has been described as treating esophageal varices, the present invention is not so limited.

While several particular forms of the invention have been illustrated and described, it will be apparent that various modifications may be made without departing from the scope of the invention. Accordingly, it is not intended that the invention be limited, except as by the appended claims.

What is claimed is:

1. A method of applying energy to cause shrinkage of a dilated vein for treating hemorrhoids, the method comprising the steps of:

introducing a catheter having a working end and means for heating located at the working end, to a treatment site in a vein;

positioning the means for heating at the treatment site in the vein;

applying energy from the means for heating to heat the treatment site and cause shrinkage of the vein;

terminating the emission of energy from the means for heating after sufficient shrinkage of the vein so as to reduce the hemorrhoid while the vein remains patent.

2. The method of claim 1, wherein the step of introducing the catheter includes the step of advancing the catheter through the iliac vein.

3. The method of claim 1, wherein the step of positioning the means for heating at the treatment site further includes the step of placing the means for heating at the treatment site so that heating of the venous valve is minimized.

4. The method of claim 1, wherein the step of positioning the means for heating further includes the step of arranging the means for heating for achieving circumferential shrinkage of the vein.

5. The method of claim 1, wherein the step of positioning the means for heating further includes the step of moving the means for heating into apposition with the vein wall at the treatment site.

6. The method of claim 1, wherein the step of positioning further includes the step of increasing an effective diameter of the catheter to place the means for heating into apposition with the vein wall; and the step of applying energy further includes the step of reducing the effective diameter of the catheter so as to maintain apposition with the vein wall as the vein wall shrinks.

7. The method of claim 1, wherein the step of applying energy further includes the step of limiting the shrinkage of the vein to a selected diameter.

8. The method of claim 1, wherein the step of applying energy further includes the step of controlling the energy from the means for heating so as to minimize coagulation in the vein.

9. The method of claim 1, wherein the step of applying energy further includes the step of controlling the energy from the means for heating so as to control the spread of heating at the treatment site of the vein.

10. The method of claim 1, further comprising the step of determining the extent of shrinkage of the vein.

11. The method of claim 10, further comprising the step of determining the extent of shrinkage of the vein using fluoroscopy.

12. The method of claim 1, further comprising the steps of positioning the means for heating at a second treatment site; and repeating the applying and terminating steps.

13. A method of applying energy to cause the shrinkage of a dilated vein for treating hemorrhoids, the method comprising the steps of:
   introducing a catheter having a working end and an electrode located at the working end, to a treatment site in the vein;
   positioning the electrode at the treatment site in the vein;
   applying radio frequency energy from the electrode to heat the treatment site and cause shrinkage of the vein;
   terminating the applying of radio frequency energy from the electrode after sufficient shrinkage of the vein so as to reduce the hemorrhoids while that the vein remains patent.

14. The method of claim 13, wherein the step of introducing the catheter includes the step of advancing the catheter through the external iliac vein.

15. The method of claim 13, wherein the step of positioning the electrode at the treatment site further includes the step of placing the electrode at the treatment site so as to minimize heating of the venous valve.

16. The method of claim 13, wherein the step of positioning the electrode further includes the step of arranging a plurality of electrodes on the catheter for achieving circumferential shrinkage of the vein and minimizing axial shortening.

17. The method of claim 13, wherein the step of positioning further comprises the step of inflating a balloon with an inflation medium so that the balloon engages the vein; wherein the step of applying energy further includes the step of heating the inflation medium by the heating means, wherein the treatment site is heated by the conduction of heat from the balloon.

18. The method of claim 13, wherein the step of positioning the electrode further includes the step of moving the electrode into apposition with the vein wall at the treatment site.

19. The method of claim 13, wherein the step of positioning further includes the step of deflecting an elongate member to place the electrode in apposition with the vein wall at the treatment site.

20. The method of claim 13, wherein the step of positioning further includes the step of inflating a balloon on the catheter to engage an elongate member, wherein the elongate member is deflected to place the electrode in apposition with the vein wall at the treatment site.

21. The method of claim 13, wherein the step of positioning the electrode at the treatment site further includes the step of inflating a balloon on the catheter to move the electrode into apposition with the vein wall.

22. The method of claim 13, wherein the step of positioning further includes the step of moving a deflection wire through the catheter to deflect the catheter and the electrode to one side of the vein at the treatment site.

23. The method of claim 13, wherein the step of positioning further includes the step of actuating a deflection wire on one side of the catheter so as to move the catheter and the electrode on the side of the catheter opposite the deflection wire to one side of the vein.

24. The method of claim 13, wherein the step of positioning further includes the step of inflating a balloon on one side of the catheter so as to move the catheter and the electrode on the other side of the catheter to one side of the vein at the treatment site.

25. The method of claim 13, wherein the step of positioning further includes the step of inflating a balloon on the catheter to center the catheter and the electrode within the vein.

26. The method of claim 13, wherein the step of applying energy further includes the step of limiting the shrinkage of the vein to a selected diameter.

27. The method of claim 13, wherein the step of applying energy further includes the step of limiting the shrinkage of the vein by inflating a balloon to a selected diameter; wherein the inflated balloon prevents shrinkage of the vein beyond the selected diameter.

28. The method of claim 13, wherein the step of positioning the electrode further includes the step of placing the electrode into apposition with the vein wall; and the step of applying energy further includes the step of reducing an effective diameter of the catheter in a controlled manner so as to maintain apposition with the vein wall as the vein wall shrinks until a diameter for the vein is achieved, wherein the vein continues to function.

29. The method of claim 13, wherein the step of positioning the electrode further includes the step of placing the electrode into apposition with the vein by increasing an effective diameter of the catheter, wherein the shrinkage of the vein reduces the effective diameter of the catheter; and
   the step of limiting the shrinkage of the vein further includes the step of preventing the effective diameter of the catheter from being reduced to less than a selected diameter representing the sufficient shrinkage of the vein.

30. The method of claim 13, wherein the step of applying energy further includes the step of limiting the shrinkage of the vein to the fixed diameter of the catheter at the working end.

31. The method of claim 13, wherein the electrode includes a plurality of longitudinal electrodes, and the step of applying the high frequency energy further includes the step of providing the high frequency energy to the longitudinal electrodes along the circumference of the working end of the catheter; wherein the vein is shrunk circumferentially and axial shrinkage of the vein is minimized.

32. The method of claim 13, wherein the electrode is a ring electrode, and the step of applying the high frequency energy further includes the step of providing radio frequency energy to the ring electrode at the working end of the catheter.

33. The method of claim 13, wherein the step of applying the high frequency energy further includes the step of providing an inert tip at the working end of the catheter past the electrode.

34. The method of claim 13, further comprising the step of delivering a cooling fluid to the treatment site for preventing thermal coagulation.

35. The method of claim 13, further comprising the step of determining the extent of shrinkage of the vein.

36. The method of claim 13, further comprising the step of determining the extent of shrinkage of the vein using fluoroscopy.

37. The method of claim 13, further comprising the step of determining the extent of shrinkage of the vein using ultrasound imaging.

38. The method of claim 13, further comprising the step of determining when to terminate the applying of radio frequency energy by measuring the time at which a specific temperature has been achieved at the treatment site.

39. A method of applying energy to cause shrinkage of a vein for restoring the competency of a venous valve in treating hemorrhoids, the method comprising the steps of:
   introducing a catheter having a working end and means for heating located at the working end, to a treatment site in a vein;
   positioning the means for heating at the treatment site in the vein;
   applying energy from the means for heating to heat the treatment site and cause shrinkage of the vein;
   terminating the emission of energy from the means for heating after sufficient shrinkage of the vein so as to restore venous valve competency and reduce the hemorrhoids.

40. A method of applying energy to cause the shrinkage of a vein for restoring the competency of a venous valve in treating hemorrhoids, the method comprising the steps of:
   introducing a catheter having a working end and an electrode located at the working end, to a treatment site in the vein;
   positioning the electrode at the treatment site in the vein;
   applying high frequency energy from the electrode to heat the treatment site and cause shrinkage of the vein;
   terminating the application of energy from the electrode after sufficient shrinkage of the vein so as to restore venous valve competency and reduce the hemorrhoids.

41. The method of claim 40, wherein the step of introducing the catheter includes the step of advancing the catheter through the iliac vein.

42. The method of claim 40, wherein the step of positioning the electrode at the treatment site further includes the step of placing the electrode at the treatment site so as to minimize heating of the venous valve.

43. The method of claim 40, wherein the step of positioning the electrode at the treatment site further includes the step of placing the electrode across the venous valves at the treatment site.

44. The method of claim 40, wherein the step of positioning the electrode at the treatment site further includes the step of introducing the catheter retrograde to venous flow and advancing the catheter to the cusps of the venous valves at the treatment site.

45. The method of claim 40, wherein the step of positioning the electrode further includes the step of arranging a plurality of electrodes on the catheter for achieving circumferential shrinkage of the vein and minimizing axial shortening.

46. The method of claim 40, wherein the step of positioning further comprises the step of inflating a balloon with an inflation medium so that the balloon engages the vein; wherein the step of applying energy further includes the step of heating the inflation medium by the heating means, wherein the treatment site is heated by the conduction of heat from the balloon.

47. The method of claim 40, wherein the step of positioning the electrode further includes the step of moving the electrode into apposition with the vein wall at the treatment site.

48. The method of claim 40, wherein the step of positioning further includes the step of deflecting an elongate member radially outward from the catheter to place the electrode in apposition with the vein wall at the treatment site.

49. The method of claim 40, wherein the step of positioning further includes the step of inflating a balloon on the catheter to deflect an elongate member, wherein the electrode is placed in apposition with the vein wall at the treatment site.

50. The method of claim 40, wherein the step of positioning further includes the step of inflating a balloon on the catheter to deflect move the electrode into contact with the vein wall at the treatment site.

51. The method of claim 40, wherein the step of positioning further includes the step of moving a deflection wire through the catheter to deflect the catheter and the electrode to one side of the vein at the treatment site.

52. The method of claim 40, wherein the step of positioning further includes the step of actuating a deflection wire on one side of the catheter to move the catheter and the electrode on the side of the catheter opposite the deflection wire to one side of the vein.

53. The method of claim 40, wherein the step of positioning further includes the step of inflating a balloon on one side of the catheter so as to move the catheter, and the electrode on the side of the catheter opposite the balloon, to one side of the vein at the treatment site.

54. The method of claim 40, wherein the step of positioning further includes the step of inflating a balloon on the catheter to center the catheter and the electrode within the vein.

55. The method of claim 40, wherein the step of applying energy further includes the step of limiting the shrinkage of the vein to a selected diameter.

56. The method of claim 40, wherein the step of applying energy further includes the step of limiting the shrinkage of the vein by inflating a balloon to a selected diameter; wherein the inflated balloon prevents shrinkage of the vein beyond the selected diameter.

57. The method of claim 40, wherein the step of positioning the electrode further includes the step of placing the electrode into apposition with the vein wall; and the step of applying energy further includes the step of reducing an effective diameter of the catheter in a controlled manner so as to maintain contact with the vein wall as the vein wall shrinks, until a selected diameter for the vein is achieved for restoring venous valve competency.

58. The method of claim 40, wherein the step of positioning the electrode further includes the step of placing the electrode into apposition with the vein by increasing an effective diameter of the catheter, wherein the shrinkage of the vein reduces the effective diameter of the catheter; and
   the step of limiting the shrinkage of the vein further includes the step of preventing the effective diameter of the catheter from being reduced to less than a selected diameter representing the sufficient shrinkage of the vein.

59. The method of claim 40, wherein the step of applying energy further includes the step of limiting the shrinkage of the vein to the fixed diameter of the catheter at the working end.

60. The method of claim 40, wherein the step of applying energy further includes the step of controlling the frequency of the energy from the electrode so as to minimize coagulation of blood in the vein.

61. The method of claim 40, wherein the step of applying energy further includes the step of controlling the frequency of the energy from the electrode so as to control the spread of heating at the treatment site of the vein.

62. The method of claim 40, wherein the step of applying energy further includes the step of controlling the frequency and total power of the energy so as to cause the external wall of the hemorrhoidal vein to become affixed to adjacent tissue.

63. The method of claim 40, wherein the step of applying the high frequency energy further includes the step of providing the high frequency energy to a plurality of longitudinal electrodes located around the circumference of the working end of the catheter.

64. The method of claim 40, wherein the step of applying the high frequency energy further includes the step of providing an inert tip at the working end of the catheter past the electrode.

65. The method of claim 40, further comprising the step of delivering a cooling fluid into the vein near the treatment site for preventing thermal coagulation.

66. The method of claim 40, further comprising the step of determining the extent of shrinkage of the vein.

67. The method of claim 40, further comprising the step of determining the extent of shrinkage of the vein using fluoroscopy.

68. The method of claim 40, further comprising the step by infusing radiopaque contrast solution through the catheter lumen to assess valve competence via descending venography.

69. The method of claim 40, further comprising the step of determining the extent of shrinkage of the vein using ultrasound imaging.

70. The method of claim 40, further comprising the step of determining when to terminate the applying of radio frequency energy by measuring the time at which a specific temperature has been achieved at the treatment site using a temperature sensor located on the electrode in contact with the vein wall.

71. The method of claim 70, further comprising the step of providing a filtering circuit to eliminate radio frequency noise from a temperature signal from the temperature sensor located on the electrode.

* * * * *